US012091389B2

(12) United States Patent
Abood et al.

(10) Patent No.: US 12,091,389 B2
(45) Date of Patent: Sep. 17, 2024

(54) PYRAZOLYLBENZENE-1,3-DIOLS FOR DISEASES ASSOCIATED WITH G PROTEIN-COUPLED RECEPTOR 18 AND IN COMBINATION WITH TRANSIENT RECEPTOR POTENTIAL VANILLOID 1

(71) Applicants: Temple University—Of The Commonwealth System of Higher Education, Philadelphia, PA (US); CONSEJO SUPERIOR DE INVESTIGACIONES CIENTÍFICAS, Madrid (ES); University of North Carolina Greensboro, Greensboro, NC (US)

(72) Inventors: Mary Ellen Abood, Philadelphia, PA (US); Eugen Brailoiu, Philadelphia, PA (US); Luciana Magalhaes Leo, Philadelphia, PA (US); Pingwei Zhao, Philadelphia, PA (US); Nadine Jagerovic, Madrid (ES); Ana Lago Fernández, Madrid (ES); Paula Morales Lazaro, Madrid (ES); Patricia Hodapp Reggio, Greensboro, NC (US); Dow Preston Hurst, Greensboro, NC (US); Nouroddin Sotoudeh Chafi, Greensboro, NC (US)

(73) Assignees: Temple University Of The Commonwealth System of Higher Education, Philadelphia, PA (US); CONSEJO SUPERIOR DE INVESTIGACIONES CIENTIFICAS, Madrid (ES); University of North Carolina Greensboro, Greensboro, SC (US)

( * ) Notice: Subject to any disclaimer, the term of this patent is extended or adjusted under 35 U.S.C. 154(b) by 0 days.

(21) Appl. No.: 17/232,321

(22) Filed: Apr. 16, 2021

(65) Prior Publication Data
US 2021/0323927 A1 Oct. 21, 2021

Related U.S. Application Data

(60) Provisional application No. 63/011,523, filed on Apr. 17, 2020.

(51) Int. Cl.
C07D 231/12 (2006.01)
C07D 401/04 (2006.01)

(52) U.S. Cl.
CPC ......... *C07D 231/12* (2013.01); *C07D 401/04* (2013.01)

(58) Field of Classification Search
CPC .............. C07D 231/12; C07D 401/04
See application file for complete search history.

(56) References Cited

PUBLICATIONS

Musante, et al. Annali di Chmica, 1955, 45, 918-42, Accession No. 1957:9338 (abstract) retrieved from STN, entered in STN on Apr. 22, 2001.*
Endometriosis: overview [online] retrieved from the internet on Jun. 24, 2022; URL: https: //www.mayoclinic.org/diseases-condition/endometriosis.*
Can I prevent endometriosis [online] retrieved from the internet on Jun. 24, 2022; URL: https://www.webmd.com/women/endometriosis/can-i-prevent-endometriosis.*
Anxiety Prevention [online] retrieved from the internet on Jun. 24, 2022; URL: https://www.healthline.com/health/anxiety-prevention.*
Anxiety Disorders [online] retrieved from the internet on Jun. 24, 2022; URL: https://www.mayoclinic.org/diseases-conditions/anxiety-disorders.*
Adamczyk et al., The Effects of Cannabinoid CB1, CB2 and Vanilloid TRPV1 Receptor Antagonists on Cocaine Addictive Behavior in Rats. Brain Res. 2012, 1444, 45-54.
Burstein et al., Resolution of Inflammation by N-Arachidonoylglycine. J. Cell. Biochem. 2011, 112 (11), 3227-3233.
Caldwell et al., A GPR18-Based Signalling System Regulates IOP in Murine Eye. Br. J. Pharmacol. 2013, 169 (4), 834-843.
Caterina et al., The Capsaicin Receptor: A Heat-Activated Ion Channel in the Pain Pathway. Nature 1997, 389 (6653), 816-824.
Chiang et al., Identification of Resolvin D2 Receptor Mediating Resolution of Infections and Organ Protection. J. Exp. Med. 2015, 212 (8), 1203-1217.
Cho et al., Inhibition of Transient Potential Receptor Vanilloid Type 1 Suppresses Seizure Susceptibility in the Genetically Epilepsy-Prone Rat. CNS Neurosci. Ther. 2018, 24 (1), 18-28.
Console Bram et al., Activation of GPR18 by Cannabinoid Compounds: A Tale of Biased Agonism. Br. J. Pharmacol. 2014, 171, 3908-3917.
Finlay et al., GPR18 Undergoes a High Degree of Constitutive Trafficking but Is Unresponsive to N-Arachidonoyl Glycine. PeerJ 2016, 4, e1835.
Flegel et al., Characterization of Non-Olfactory GPCRs in Human Sperm with a Focus on GPR18. Sci. Rep. 2016, 6 (Aug. 2015), 32255.
Gantz et al., Cloning and Chromosomal Localization of a Gene (GPR18) Encoding a Novel Seven Transmembrane Receptor Highly Expressed in Spleen and Testis. Genomics 1997, 42 (3), 462-466.
Grabiec et al., Protective Effect of N-Arachidonoyl Glycine-GPR18 Signaling after Excitotoxical Lesion in Murine Organotypic Hippocampal Slice Cultures. Int. J. Mol. Sci. 2019, 20 (6), 1266.
Gram et al., TRPV1: A Potential Therapeutic Target in Type 2 Diabetes and Comorbidities? Trends Mol. Med. 2017, 23 (11), 1002-1013.
Guerrero-Alba et al., Some Prospective Alternatives for Treating Pain: The Endocannabinoid System and Its Putative Receptors GPR18 and GPR55. Front. Pharmacol. Jan. 9, 2019, 1-20.

(Continued)

*Primary Examiner* — Shawquia Jackson
(74) *Attorney, Agent, or Firm* — Riverside Law LLP

(57) ABSTRACT

The present invention relates to pyrazolylbenzene-1,3-diols as cannabidiol derivatives, its use for the manufacture of a medicament, and more particularly, to the use of this medicament for the treatment and/or prevention of a disorder associated with the GPR18 and/or TRPV1 receptors and the use of these compounds for pharmacological assays related to GPR18 and/or TRPV1.

17 Claims, 4 Drawing Sheets

(56) References Cited

PUBLICATIONS

Ago-Fernandez et al., New Methods for the Synthesis of Cannabidiol Derivatives. In Cannabinoids and Their Receptors; Reggio, P. H., Ed.; Academic Press: Burlington, 2017; vol. 593, pp. 237-257.
Malek et al., The Multiplicity of Spinal AA-5-HT Anti-Nociceptive Action in a Rat Model of Neuropathic Pain. Pharmacol. Res. 2016, 111, 251-263.
Matouk et al., The Effect of Chronic Activation of the Novel Endocannabinoid Receptor GPR18 on Myocardial Function and Blood Pressure in Conscious Rats. J. Cardiovasc. Pharmacol. 2017, 69 (1), 23-33.
McHugh et al., N-Arachidonoyl Glycine, an Abundant Endogenous Lipid, Potently Drives Directed Cellular Migration through GPR18, the Putative Abnormal Cannabidiol Receptor. BMC Neurosci. 2010, 11, 44.
McHugh et al., Δ 9-Tetrahydrocannabinol and N-Arachidonyl Glycine Are Full Agonists at GPR18 Receptors and Induce Migration in Human Endometrial HEC-1B Cells. Br. J. Pharmacol. 2012, 165 (8), 2414-2424.
Miller et al., Evidence for a GPR18 Role in Diurnal Regulation of Intraocular Pressure. Investig. Ophthalmol. Vis. Sci. 2016, 57 (14), 6419-6426.
Pascoal et al., Resolvin RvD2 Reduces Hypothalamic Inflammation and Rescues Mice from Diet-Induced Obesity. J. Neuroinflammation 2017, 14 (1), 1-12.
Penumarti et al., The Novel Endocannabinoid Receptor GPR18 Is Expressed in the Rostral Ventrolateral Medulla and Exerts Tonic Restraining Influence on Blood Pressure. J. Pharmacol. Exp. Ther. 2014, 349 (1), 29-38.

Qin et al., Quantitative Expression Profiling of G-Protein-Coupled Receptors (GPCRs) in Metastatic Melanoma: The Constitutively Active Orphan GPCR GPR18 as Novel Drug Target. Pigment Cell Melanoma Res. 2011, 24 (1), 207-218.
Rajaraman et al., G Protein Coupled Receptor 18: A Potential Role for Endocannabinoid Signaling in Metabolic Dysfunction. Mol. Nutr. Food Res. 2016, 60 (1), 92-102.
Rempel et al., Bicyclic Imidazole-4-One Derivatives: A New Class of Antagonists for the Orphan G Protein-Coupled Receptors GPR18 and GPR55. Medchemcomm 2014, 5 (5), 632-649.
Rosenkilde et al., Molecular Pharmacological Phenotyping of EBI2: An Orphan Seven-Transmembrane Receptor with Constitutive Activity. J. Biol. Chem. 2006, 281 (19), 13199-13208.
Schoeder et al., Structure-Activity Relationships of Imidazothiazinones and Analogs as Antagonists of the Cannabinoid-Activated Orphan G Protein-Coupled Receptor GPR18. Eur. J. Med. Chem. 2018, 155, 381-397.
Simcocks et al., Atypical Cannabinoid Ligands O-1602 and O-1918 Administered Chronically in Diet-Induced Obesity. Endocr. Connect. 2019, 8 (3), 203-216.
Socała et al., Evaluation of the Antidepressant- and Anxiolytic-like Activity of α-Spinasterol, a Plant Derivative with TRPV1 Antagonistic Effects, in Mice. Behav. Brain Res. 2016, 303, 19-25.
Tominaga et al., The Cloned Capsaicin Receptor Integrates Multiple Pain-Producing Stimuli. Neuron 1998, 21 (3), 531-543.
Zhang et al. GPR18 expression on PMNs as biomarker for outcome in patient with sepsis, Life Sciences 2019, 217 49.

\* cited by examiner

PYRAZOLYLBENZENE-1,3-DIOLS FOR DISEASES ASSOCIATED WITH G PROTEIN-COUPLED RECEPTOR 18 AND IN COMBINATION WITH TRANSIENT RECEPTOR POTENTIAL VANILLOID 1

CROSS-REFERENCE TO RELATED APPLICATIONS

This application claims priority to U.S. Provisional Application No. 63/011,523, filed Apr. 17, 2020, the disclosure of which is hereby incorporated by reference in its entirety.

STATEMENT REGARDING FEDERALLY SPONSORED RESEARCH OR DEVELOPMENT

This invention was made with government support under DA045698 awarded by the National Institutes of Health. The government has certain rights in the invention.

FIELD OF THE INVENTION

The present invention relates to pyrazolylbenzene-1,3-diols as cannabidiol derivatives, its use for the manufacture of a medicament, and more particularly, to the use of this medicament for the treatment and/or prevention of a disorder associated with the GPR18 and/or TRPV1 receptors and the use of these compounds for pharmacological assays related to GPR18 and/or TRPV1. Therefore, the present invention is in the field of pharmacology.

BACKGROUND ART

G Protein-coupled receptor 18 (GPR18) has been related to the endocannabinoid system due to its interactions with cannabinoids such a cannabidiol, ab-normal cannabidiol, $\Delta^9$tetrahydrocannabinoid. The Nomenclature Committee of the Union of Basic and Clinical Pharmacology (NC-IUPHAR) classifies GPR18 as an orphan receptor due to incomplete evidence of specific endogenous ligands. N-Arachidonoyl glycine (NAGly) has been suggested to be an endogenous ligand for GPR18 (Console Bram et al. Br. J. Pharmacol. 2014, 171, 3908). The endogenous lipid mediator resolvin D2 (RvD2) has also been proposed as endogenous agonist of GPR18 (Chiang, N. et al. J. Exp. Med. 2015, 212, 1203). This receptor is expressed within the central nervous system including striatum, cerebral cortex, hippocampus and cerebellum. GPR18 is also highly expressed in lymphoid tissues such as the spleen and thymus, as well as bone marrow, peripheral immune cells, peripheral organs (testes, lung, skin) and the retina.

The receptor GPR18 contributes to directed microglial migration involved in the defense of the central nervous system, in the homeostatic maintenance and in tissue which produces pro-inflammation and cytotoxicity implicated in several neurodegenerative diseases, including multiple sclerosis and Alzheimer's disease (McHugh et al. BMC Neuroscience 2010, 11:44).

Another therapeutic application that has been suggested for GPR18 modulators is endometriosis disorder since there is evidence that endogenous and phytocannabinoids regulate human endometrial cell migration through a GPR18 signalling mechanism (Mc Hugh et al. Br. J. Pharmacol. (2012) 165 2414).

In a mouse peritonitis model, the putative GPR18 endogenous ligand NAGly showed anti-inflammatory activity which GPR18 contribution has been evidence in cell culture models by apoptosis of inflammatory leukocytes (Burstein et al. Cell. Biochem. 2011, 113, 3227).

There is evidence that acute inflammation triggered by infectious agents involves GPR18 receptor. Thus, GPR18 has been proposed as a therapeutic target to control bacterial infections and promote organ protection (Zhang et al. Life Sciences 2019, 217 49).

GPR18 is suggested to play a potential role for endocannabinoid signaling in metabolic dysfunction such as obesity and diabetes. For instance, GPR18 expressed in hypothalamic proopiomelanocortin and neuropeptide-Y neurons has been reported to be involved in diet-induced hypothalamic inflammation and dietary fats (Rajaraman et al. Mol. Nutr. Food Res. 2016, 60, 92).

It has also been reported that activation of GPR18 lowers intraocular pressure and that the receptor is present in anterior eye tissues. Thus, GPR18 ligands could have therapeutic applications in glaucoma disease (Miller et al. Investig. Ophthalmol. Vis. Sci. 2016, 57, 6419).

Studies on the implication of GPR18 in physiological processes of human spermatozoa suggest a potential role of GPR18 in sperm physiology, particularly immediately prior to fertilization revealing an application in male reproduction (Flegel et al. Sci. Rep. 2016, 6, 32255).

GPR18 has also been reported to be involved in cancer. For instance, GPR18 has been considered as potential novel anticancer target in metastatic melanoma (Qin et al. Pigment Cell Melanoma Res. 2011, 24, 207).

The cardiovascular role for GPR18 has been evidenced by the action of Abn-CBD at GPR18 that causes reduction in rostral ventrolateral medulla oxidative stress and blood pressure, thus, converting GPR18 as a molecular target for developing new antihypertensive drugs that improve cardiac function (Penumarti et al. J. Pharmacol. Exp. Ther. 2014, 349, 29-38).

More recently, GPR18 has been suggested as an alternative biological target for pain relieve. For instance, nerve injury enhances expression of GPR18 mRNA in spinal cord and/or the dorsal root ganglia of rats, suggesting a potential role of GPR18 in the modulation of neuropathic pain (Malek et al. Pharmacol. Res. 2016, 111, 251).

Phytocannabinoids and endogenous cannabinoids have been reported to modulate the action of GPR18. However, very few potent and selective GPR18 synthetic ligands have been described so far.

On the other hand, the transient receptor potential vanilloid 1(TRPV1) is a cation channel with high permeability for $Ca^{2+}$. TRPV1 is activated by a large variety of physical and chemical stimuli such as heat, capsaicin, and resiniferatoxin. It is critically involved in sensory and pain perception. Thus, several clinical assays have been realized with TRPV1 antagonists for pain of acute migraine (clinicaltrial.gov number NCT002269022), for tooth extraction (clinicaltrial.gov number NCT00281684), and for retrosternal pain in children (clinicaltrial.gov number NCT00677378) among others type of pain. Targeting TRPV1 in diabetes type-2 results in improving insulin secretion, minimizing insulin resistance, and interfering on the disease progression in animal models (Gram et al. Trends Mol. Med. 2017, 23 1002). The translation to humans is currently ongoing with clinical trial (clinicaltrial.gov number NCT03278158) using a TRPV1 antagonist in patients with diabetes mellitus type-2 disorders. TRPV1 plays also an important role in neurological and psychiatric disorders such as epilepsy (Cho et al. CNS Neurosci. Ther. 2018, 24, 18), anxiety and depression (Socala et al. Behav. Brain Res. 2016, 303, 19), and drug-addiction disorders (Adamczyk et al. Brain Res. 2012, 1444, 45).

SUMMARY OF THE INVENTION

The invention relates to a compound of formula (I) defined in the description and in the claims useful for therapy and/or prophylaxis in a mammal, and in particular to compounds those are preferential ligands of GPR18 or have dual activity on GPR18 and TPRV1.

In one aspect, the present invention relates to a compound of general formula (I)

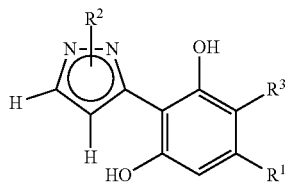

Formula (I)

or a tautomer, a pharmaceutically acceptable salt or solvate thereof;
wherein:

$R^1$ is selected from hydrogen or a substituted or unsubstituted alkyl $C_1$-$C_9$ alkyl;

$R^2$ is selected from hydrogen, substituted or unsubstituted $C_1$-$C_6$ alkyl, substituted or unsubstituted $C_1$-$C_{20}$ aryl, substituted or unsubstituted arylalkyl, substituted or unsubstituted cycloalkyl, or substituted or unsubstituted heterocyclic ring.

$R^3$ is selected from hydrogen or halogen;

with the proviso of the compounds 2-(1H-pyrazol-3-yl)benzene-1,3-diol and 5-pentyl-2-(1H-pyrazol-5-yl)benzene-1,3-diol.

In a preferred embodiment, $R^1$ is a $C_1$-$C_9$ alkyl selected from methyl, ethyl, iso-propyl, pentyl, and 1,1-dimethyl heptyl. Even more preferred $R^1$ is methyl, pentyl or 1,1-dimethyl heptyl.

In another preferred embodiment, $R^1$ is hydrogen.

In another preferred embodiment, $R^2$ is a $C_1$-$C_6$ alkyl group; even more preferred $R^2$ is a $C_1$-$C_4$ alkyl group selected from methyl, ethyl, iso-propyl, tert-butyl; and more preferably $R^2$ is methyl or iso-propyl.

In another preferred embodiment, $R^2$ is a cycloalkyl selected from cyclopropyl, cyclopentyl and cyclohexyl; and more preferably $R^2$ is cyclohexyl.

In another preferred embodiment, $R^2$ is hydrogen.

In another preferred embodiment, $R^2$ is an aryl group selected from phenyl, naphthyl, diphenyl, indenyl, phenanthryl or anthracyl; and more preferably $R^2$ is a phenyl; even more preferred $R^2$ is a phenyl substituted by a hydroxyl or a methoxy group.

In another preferred embodiment, $R^2$ is an arylalkyl group, and more preferably substituted or unsubstituted benzyl.

In another preferred embodiment, $R^3$ is hydrogen or fluorine.

In another preferred embodiment, the compound of formula (I) is a compound of general formula (II)

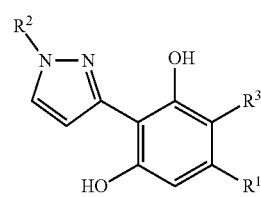

Formula (II)

or a tautomer, a pharmaceutically acceptable salt, or solvate thereof; where $R^1$, $R^2$, and $R^3$ are as defined above.

In another preferred embodiment, the compound of formula (I) is a compound of general formula (III)

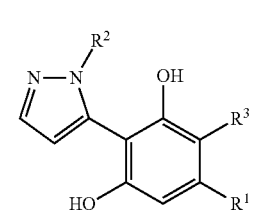

Formula (III)

or a tautomer, a pharmaceutically acceptable salt, or solvate thereof; where $R^1$, $R^2$, and $R^3$ are as defined above,
with the proviso of the compounds 2-(1H-pyrazol-3-yl)benzene-1,3-diol and 5-pentyl-2-(1H-pyrazol-5-yl)benzene-1,3-diol.

According to a preferred embodiment, the compound of formula (I) is selected from the following list:
5-pentyl-2-(1-phenyl-1H-pyrazol-5-yl)benzene-1,3-diol
2-(1-methyl-1H-pyrazol-5-yl)-5-pentylbenzene-1,3-diol
2-(1-benzyl-1H-pyrazol-3-yl)-5-pentylbenzene-1,3-diol
2-(1-benzyl-1H-pyrazol-5-yl)-5-pentylbenzene-1,3-diol
5-(2-methyloctan-2-yl)-2-(1H-pyrazol-3-yl)benzene-1,3-diol
2-(1-isopropyl-1H-pyrazol-5-yl)-5-pentylbenzene-1,3-diol
2-(1-isopropyl-1H-pyrazol-5-yl)-5-(2-methyloctan-2-yl)benzene-1,3-diol
2-(1-isopropyl-1H-pyrazol-3-yl)-5-(2-methyloctan-2-yl)benzene-1,3-diol
2-(1-isopropyl-1H-pyrazol-3-yl)benzene-1,3-diol
2-(1-isopropyl-1H-pyrazol-5-yl)benzene-1,3-diol
2-(1-isopropyl-1H-pyrazol-3-yl)-5-methylbenzene-1,3-diol
2-(1-isopropyl-1H-pyrazol-5-yl)-5-methylbenzene-1,3-diol
2-(1-isopropyl-1H-pyrazol-3-yl)-5-pentylbenzene-1,3-diol
2-(1-benzyl-1H-pyrazol-3-yl)-5-methylbenzene-1,3-diol
2-(1-benzyl-1H-pyrazol-5-yl)-5-methylbenzene-1,3-diol
2-(1-cyclohexyl-1H-pyrazol-5-yl)-5-pentylbenzene-1,3-diol
2-(1-(tert-butyl)-1H-pyrazol-3-yl)-5-pentylbenzene-1,3-diol
2-(1-(tert-butyl)-1H-pyrazol-5-yl)-5-pentylbenzene-1,3-diol
2-(1-ethyl-1H-pyrazol-3-yl)-5-pentylbenzene-1,3-diol
2-(1-ethyl-1H-pyrazol-5-yl)-5-pentylbenzene-1,3-diol
5-methyl-2-(1H-pyrazol-3-yl)benzene-1,3-diol
2-(1-cyclohexyl-1H-pyrazol-3-yl)-5-methylbenzene-1,3-diol
2-(1-cyclohexyl-1H-pyrazol-5-yl)-5-methylbenzene-1,3-diol
2-(1-ethyl-1H-pyrazol-3-yl)-5-methylbenzene-1,3-diol
2-(1-ethyl-1H-pyrazol-5-yl)-5-methylbenzene-1,3-diol
5-methyl-2-(1-(pyridin-4-ylmethyl)-1H-pyrazol-5-yl)benzene-1,3-diol
2-(1-benzyl-1H-pyrazol-3-yl)-4-fluoro-5-pentylbenzene-1,3-diol 2-(1-(3-hydroxybenzyl)-1H-pyrazol-3-yl)-5-pentylbenzene-1,3-diol 2-(1-(3-hydroxybenzyl)-1H-pyrazol-5-yl)-5-pentylbenzene-1,3-diol 2-(1-(4-hydroxybenzyl)-1H-pyrazol-5-yl)-5-pentylbenzene-1,3-diol 2-(1-(4-hydroxybenzyl)-1H-pyrazol-3-yl)-5-pentylbenzene-1,3-diol In the present invention, the term "alkyl" refers to a straight or branched hydrocarbon chain radical consisting solely of carbon and hydrogen atoms, containing no unsaturation, having from one to nine carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "C1-9 alkyl" refers to an alkyl group as defined above having up to 9 carbon atoms, optionally substituted by at least one of the substituents as defined.

In the present invention, the term "aryl" refers to aromatic radicals having in the range of 5 up to 20 carbon atoms such as phenyl, naphthyl, diphenyl, indenyl, phenanthryl or anthracyl. Preferably the aryl group has 5 to 7 carbon atoms and more preferably the aryl group is a phenyl. The aryl radicals may be optionally substituted by one or more substituents such as ($C_1$-$C_6$) alkyl, alkoxy, halogen, hydroxyl or carboxylic acid and more preferably the aryl group is substituted by one or two hydroxyl groups.

In the present invention, the term "arylalkyl" refers to an aryl group as defined above directly bonded to an alkyl group as defined above, e.g., —$CH_2C_6H_5$ and —$C_2H_5C_6H_5$.

In the present invention, the term "cycloalkyl" refers, in the present invention, to cyclic hydrocarbon chain radicals, preferably with 3 to 6 carbon atoms, and more preferably 6, which is saturated or partially saturated, and which consists only of carbon and hydrogen atoms, such as cyclopropyl, cyclopentyl or cyclohexyl and which may be optionally substituted by one or more groups such as alkyl, halogens, hydroxyl, amines, amides, cyano etc.

In the present invention, the term "heterocyclic ring" refers to a non-aromatic 3 to 8-member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

In the present invention, the term "halo", "halide", or, alternatively, "halogen" means fluoro, chloro, bromo or iodo.

In the present invention, the term "substituted" unless otherwise specified, refers to substitution with any one or any combination of the following substituents which may be the same or different and are independently selected from hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted.

In the present invention, the term "tautomer" or "tautomeric form", as used herein, refers to structural isomers of different energies that are interconvertible via a low energy barrier. For example, proton tautomers (also known as prototropic tautomers) including interconversions by the migration of a proton, such as keto-enolic or imine-enamine isomerizations. Valence tautomers include interconversions by rearrangement of some binding electrons.

In the present invention, the term "pharmaceutically acceptable salts or solvates" refers to any pharmaceutically acceptable salt, ester, solvate, or any other compound which, when administered to a recipient is capable of providing (directly or indirectly) a compound as described herein document. However, it will be appreciated that pharmaceutically unacceptable salts are also within the scope of the invention since they may be useful in the preparation of pharmaceutically acceptable salts. The preparation of salts and derivatives may be carried out by methods known in the art.

Unless otherwise noted, the compounds of the invention also relate to including compounds which differ only in the presence of one or more isotopically enriched atoms. For example, compounds having the present structures, with the exception of the substitution of a hydrogen by a deuterium or by tritium, or the substitution of a carbon by a $^{13}C$ or $^{14}C$ enriched carbon or a $^{15}N$ enriched nitrogen, are within the scope of this invention.

For example, pharmaceutically acceptable salts of compounds provided herein are synthesized by conventional chemical methods from an original compound containing a basic moiety or acid. Generally, such salts are prepared, for example, by reacting the acid or free base forms of the compounds with a stoichiometric amount of the appropriate base or acid in water or in an organic solvent or a mixture of the two. Generally, non-aqueous media such as ether, ethyl acetate, ethanol, isopropanol or acetonitrile are preferred. Examples of acid addition salts include mineral acid addition salts such as, for example, hydrochloride, hydrobromide, hydroiodide, sulfate, nitrate, phosphate and organic acid addition salts such as, for example, acetate, maleate, fumarate, citrate, oxalate, succinate, tartrate, malate, mandelate, methanesulfonate and p-toluenesulfonate. Examples of base addition salts include inorganic salts such as, for example, sodium, potassium, calcium, ammonium, magnesium, aluminum and lithium salts, and salts of organic bases such as, for example, ethylenediamine, ethanolamine, N,N-dimethylethanolamine, triethanolamine, glucamine and salts of basic amino acids.

Particularly preferred derivatives are those which increase the bioavailability of the compounds of this invention when such compounds are administered to a patient (for example, by causing a compound administered orally to be more readily absorbed into the blood), or potentiating the release of the original compound in a biological compartment (e.g. brain or lymphatic system) relative to the original species.

The compounds of formula (I), (II) or (III) may be in crystalline form as free compounds or as solvates and both forms are intended to be within the scope of the present invention. Methods of solvation are generally known within the art. Suitable solvates are pharmaceutically acceptable solvates. In a particular embodiment, the solvate is a hydrate.

The compounds of formula (I), of formula (II) and of formula (III) or their salts or solvates are preferably in a pharmaceutically acceptable form or substantially pure.

By pharmaceutically acceptable form is meant, inter alia, that they have a pharmaceutically acceptable level of purity excluding normal pharmaceutical additives such as diluents and carriers, and not including material considered toxic at normal dosage levels. The purity levels for the active ingredient are preferably above 50%, more preferably above 70%, more preferably above 90%. In a preferred embodiment, they are greater than 95% of the compound of formula (I), or salts thereof.

In a particular embodiment there is a process for the production of compounds of formula (I), formula (II) and formula (III) defined above. Said process comprises a combination of synthetic reactions known in the art such as those mentioned in the Book "Methodology in Enzymology" at the Chapter "Cannabinoids and Their receptors" (V593) Lago-Fernandez et al., 237-257.

In another aspect, the present invention relates to the use of a compound of formula (I), of formula (II) or of formula (III) for the manufacture of a medicament. In another aspect, the present invention relates to the use of a compound of formula (I), of formula (II) or of formula (III) for the manufacture of a medicament for the treatment and/or prevention of a disorder associated with GPR18 receptors.

According to a preferred embodiment, the disorder associated with GPR18 receptors is selected from neurodegenerative diseases, endometriosis, peritonitis, metabolic dysfunction, obesity-related disease, diabetes, bacterial infection, cardiovascular disease, pain, glaucoma, metastatic melanoma, and male reproduction.

In another aspect, the present invention relates to a compound of formula (I) or formula (II) or formula (III) for use in the treatment of and/or prevention of a disorder associated with TRPV1 receptors selected from pain, diabetes type-2, epilepsy, anxiety, depression, and drug-addiction.

The term "disorder" as used in the present invention refers to the presence of a behavior or group of symptoms identifiable in clinical practice, which in most cases are accompanied by discomfort or interfere with the habitual activity of the individual.

The compounds of formula (I), of formula (II) or of formula (III), their pharmaceutically acceptable salts or solvates thereof, can therefore be used in the prevention and/or treatment of a disorder requiring modulation of the GPR18 and/or TRPV1 receptors. Pharmaceutical compositions containing a therapeutically effective amount of a compound of formula (I) or formula (II), their pharmaceutically acceptable salts or solvates thereof, together with the pharmaceutically acceptable excipients constitute a further aspect of the present invention.

The amount of the compound of formula (I), formula (II) or formula (III), the pharmaceutically acceptable salts or solvates thereof, therapeutically effective to be administered as well as its dosage for treating a disease state with said compounds will depend on numerous factors, including age, patient status, severity of disease, route and frequency of administration, modulator compound to be used, etc. In another aspect, the present invention also relates to pharmaceutical compositions comprising at least one compound of the invention, or a tautomer, a pharmaceutically acceptable salt, a solvate or a prodrug thereof, together with a pharmaceutically acceptable carrier or carrier, an excipient or a vehicle, for administration to a patient.

In a preferred embodiment, the pharmaceutical composition further comprises another active ingredient.

Some examples of the pharmaceutical compositions are solids (tablets, pills, capsules, granular solid, etc.) or liquids (solutions, suspensions or emulsions) prepared for oral, nasal, topical or parenteral administration.

In a preferred embodiment of the present invention, the pharmaceutical compositions are suitable for oral administration, in solid or liquid form. Possible forms for oral administration are tablets, capsules, syrups or solutions and may contain conventional excipients known in the pharmaceutical field as binders (e.g. syrup, acacia, gelatin, sorbitol, tragacanth or polyvinyl pyrrolidone), fillers (e.g. lactose, sugar, corn starch, calcium phosphate, sorbitol or glycine), disintegrating agents (e.g. starch, polyvinyl pyrrolidone or microcrystalline cellulose) or a pharmaceutically acceptable surfactant such as sodium lauryl sulfate.

Compositions for oral administration may be prepared by the conventional methods of Galenic Pharmacy as a mixture and dispersion. The tablets may be coated following methods known in the pharmaceutical industry.

The pharmaceutical compositions may be adapted for parenteral administration, as sterile solutions, suspensions, or lyophilizates of the products of the invention, using the appropriate dosage. Suitable excipients may be employed, such as pH buffering agents or surfactants.

Administration of the compounds or compositions of the present invention may be accomplished by any suitable method, such as intravenous infusion and oral, intraperitoneal or intravenous routes. Oral administration is preferred because of the convenience of patients and the chronic nature of the diseases to be treated. The administered amount of a compound of the present invention will depend upon the relative efficacy of the compound selected, the severity of the disease to be treated and the patient's weight. However, the compounds of this invention will be administered one or more times a day, for example 1, 2, 3 or 4 times daily, with a total dose between 0.1 and 1000 mg/kg/day. It is important to note that dose variations may be necessary, depending on the patient's age and condition, as well as changes in the route of administration.

The compounds and compositions of this invention may be used alone or in combination with other drugs to provide a combination therapy. The other drugs may form part of the same composition, or be provided as a separate composition, for administration at the same time or at a different time.

A combination therapy may be of particular interest because of the type of pathologies to be treated with these compounds as defined herein, these pathologies are especially complex, since patients generally exhibit a combination of symptoms as well as a variety of damages or alterations. Therefore, it may be of interest to combine several drugs, each directed to specifically prevent, alleviate or cure a particular symptom, damage or alteration, or also to several of them, resulting in a combined therapy directed at the disease or condition of a form global, taking into account many, most, or all aspects involved in it.

Drugs to be combined with the compounds of the present invention may be approved drugs for the treatment of any of the diseases, or be newly developed.

In another aspect, the present invention relates to the use of a compound of formula (I), of formula (II) or of formula (III) for the manufacture of a reagent in biological assays related to GPR18 and/or TRPV1 receptor.

In the present invention, the term "reagent" refers to a test substance which is added to a system to give rise to a reaction or to check whether a reaction occurs.

In the present invention, the term "biological assay" refers to a method for measuring a substance, either quantitatively or qualitatively, in a living or in vitro organism. Qualitative tests are used to determine the physical effects of a substance in that organism. Quantitative tests are used for the estimation of the concentration or potency of a substance by measuring the biological response produced by that substance.

Throughout the description and claims the word "comprises" and its variants are not intended to exclude other technical features, additives, components or steps. Other objects, advantages and features of the invention will be apparent to those skilled in the art in part from the description and in part from the practice of the invention. The following examples and figures are given by way of illustration and are not intended to be limiting of the present invention.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings are provided by way of illustration and are not intended to be limiting of the present invention.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

EXPERIMENTAL EXAMPLES

Figure 1:
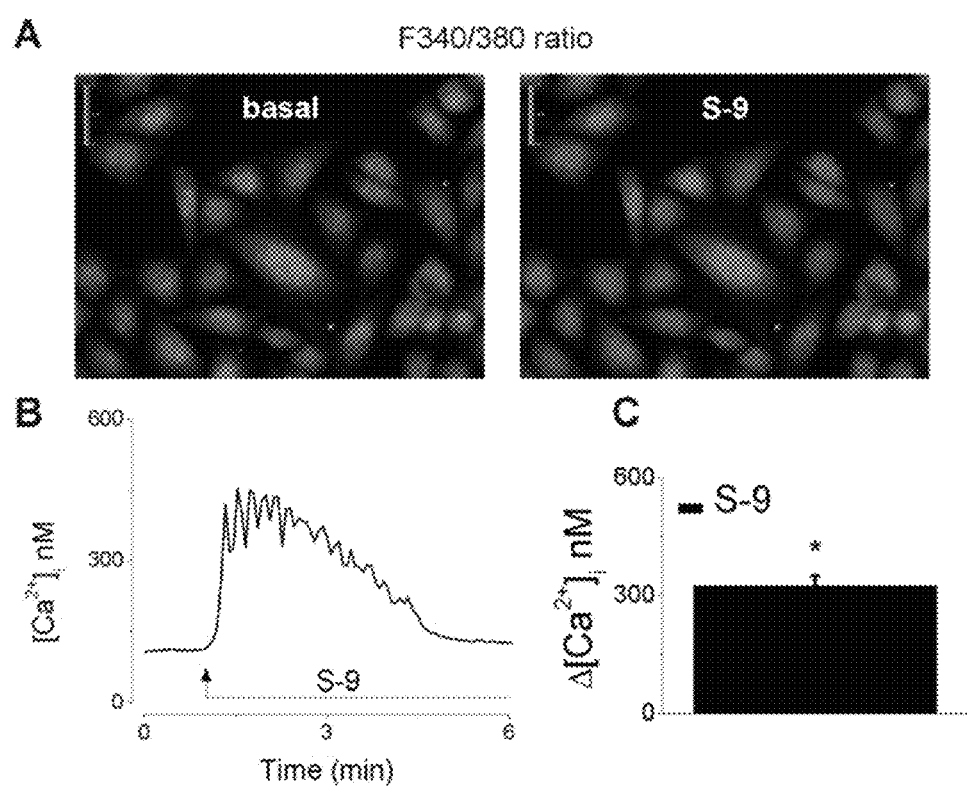
FIG. 1. Effect of S9 (10 µM) on intracellular calcium ($Ca^{2+}$) in a GPR18 expressing cell line. A. F340/F380 ratio before (basal) and after treatment with 10 µM S9. B. S9-induced increase in $[Ca^{2+}]_i$. C. Quantification of response. n=45-50 cells.

The invention will now be illustrated by assays carried out by the inventors, which shows the effectiveness of the product of the invention.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1. General Methods of Preparation

The compounds claimed in the present invention have a 2-(1H-pyrazol-5(2)-yl)benzene-1,3-diol as scaffold. Compounds such as 2-(1H-pyrazol-3-yl)benzene-1,3-diol and 5-pentyl-2-(1H-pyrazol-5-yl)benzene-1,3-diol have been previously disclosed with no biological activity (Lago-Fernandez et al. In Methods in enzymology 2017, 593, 237).

Purification of the reaction products was performed by column chromatography using silica gel 60 Merck 230-400 mesh. The separation by semi-preparative high-performance liquid chromatography was performed on a Waters chromatograph integrated by a 2767 Sample Manager injector/manifold module, a System Fluidic Organizer separation module, a Photodiode Array 2998 (UV-visible) detector and a mass spectrophotometer 3100 Mass Detector. A SunFire™ 018 reverse phase column (19 mm×150 mm) is used for the separation. The mobile phases used are: A (MeCN+0.1% formic acid) and B ($H_2O$+0.1% formic acid). The gradient was performed using a flow of 24 mL/min in 70 minutes monitoring at λ=254 nm. Exact mass spectra were recorded on an Agilent Technologies 6520 Accurate-Mass QTOF LC/MS spectrometer with a positive electrospray source. NMR analyzes were performed in the deuterated solvent indicated in each case. $^{13}$C-NMR, heteronuclear correlation HMBC and HSQC were recorded on a Mercury 400 (400 and 101 MHz) or Varian 500 (500 and 126 MHz) spectrometers at 25° C. The melting points were measured on an MP70 Mettler Toledo apparatus.

A process is described in Scheme (1) for the preparation of compounds of general formula I, wherein $R^1$, $R^2$ and $R^3$ have the meanings defined above.

This process is carried out as described below:

The compounds of general formula (I) of the present invention were synthesized from 5-hydroxy-4H-chromen-4-one, 5-hydroxy-7-methyl-4H-chromen-4-one, 5-hydroxy-7-pentyl-4H-chromen-4-one, or 5-hydroxy-7-(1,1-dimethylheptyl-1-yl)-4H-chromen-4-one that was treated with hydroxylamine hydrochloride or the corresponding substituted hydrazine in ethanol to get a mixture of two 5-alkyl-2-(1H-pyrazol-5-yl)benzene-1,3-diol regioisomers that could be easily separated by chromatography on silica gel.

To synthesize the said 5-hydroxy-4H-chromen-4-ones, the corresponding 1-(2,6-dihydroxy-4-alkylphenyl)ethan-1-one was cyclized with perchloric acid and triethyl orthoformate at room temperature or with boron trifluoride diethyl etherate and methanesulfonyl chloride at 90° C. as illustrated on Scheme (1). 5-Hydroxy-7-pentyl-4H-chromen-4-one and 5-hydroxy-7-(1,1-dimethylheptyl-1-yl)-4H-chromen-4-one were previously prepared by acylation of 5-pentylbenzene-1,3-diol or 5-(1',1'-dimethylheptyl-1-yl)benzene-1,3-diol with aluminium chloride and acyl chloride in dichloromethane under inert atmosphere at 0° C. (Scheme (1)).

Scheme (1)

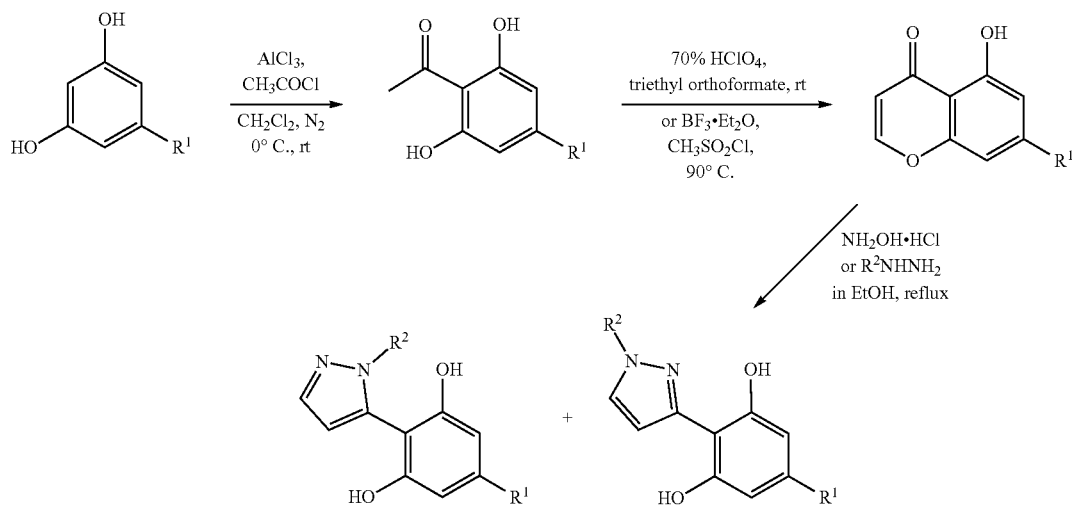

Additionally, compounds of formula I wherein $R^3$ is a fluorine atom can be obtained from their parent compounds wherein $R^3$ is hydrogen under the reaction conditions described in scheme (2).

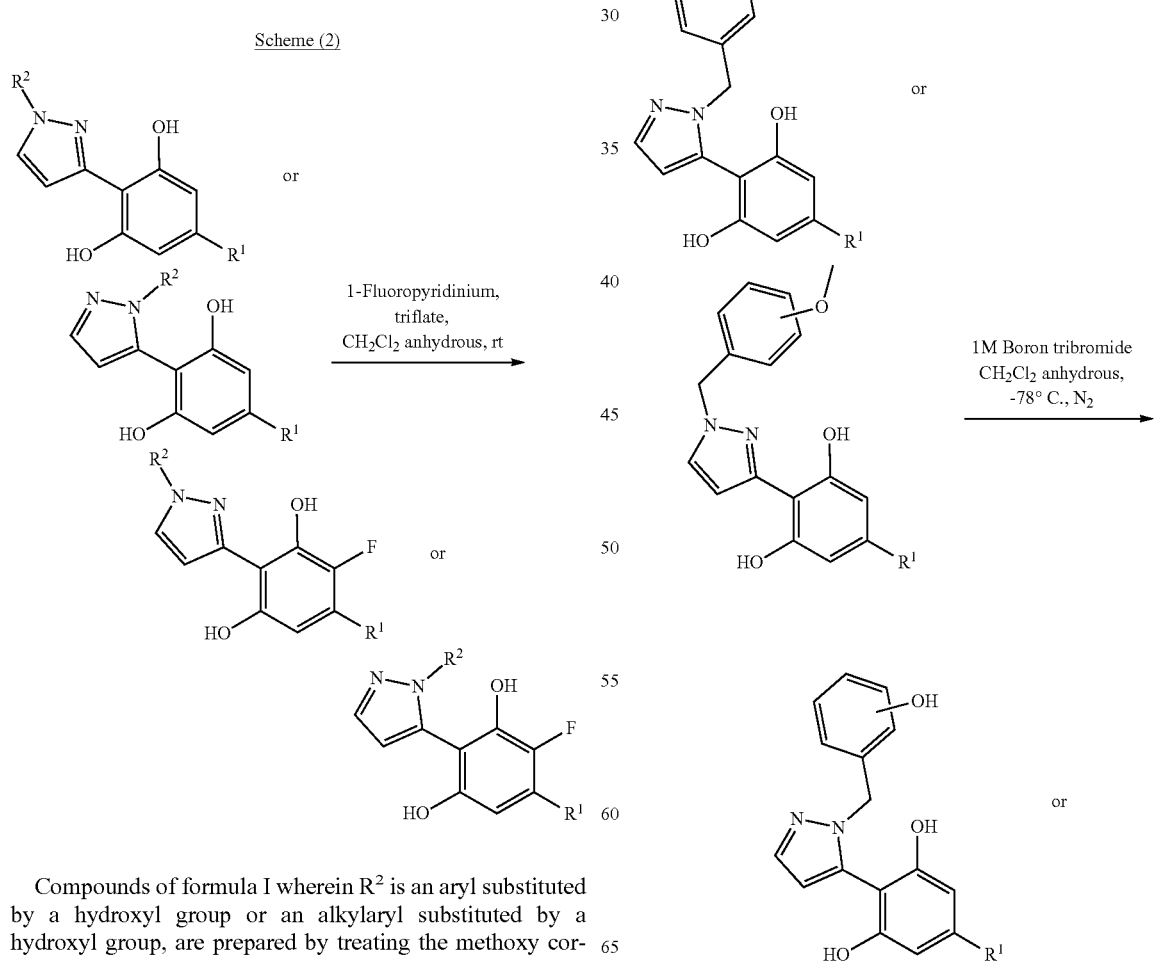

Compounds of formula I wherein $R^2$ is an aryl substituted by a hydroxyl group or an alkylaryl substituted by a hydroxyl group, are prepared by treating the methoxy corresponding derivatives with boron tribromide as exemplified in scheme (3).

-continued

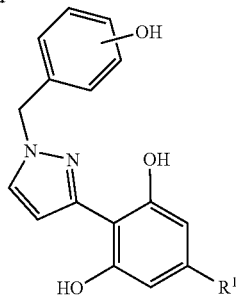

Intermediates 1-(2,6-Dihydroxy-4-pentylphenyl)ethan-1-one

To a suspension of aluminum chloride (4.43 g; 33.3 mmol) in dichloromethane, a solution of commercially available olivetol (3.00 g; 16.7 mmol) in dichloromethane was added at 0° C. under a $N_2$ atmosphere and stirred for 20 min. Then, acyl chloride (2.36 mL, 33.3 mmol) was added dropwise, and the reaction was stirred at room temperature for 20 min. Afterwards, the reaction was added to a beaker containing HCl 1 N in water/ice, and the organic layer was extracted with dichloromethane, dried over $MgSO_4$ and the solvent was removed under vacuum. The crude mixture was purified by column chromatography (dichloromethane/hexane, 4:1), resulting in a yellow oil (1.32 g, yield=44%): 1H-NMR (400 MHz, CDCl3) δ: 6.15 (s, 2H, 3-H and 5-H), 2.64 (s, 3H, 2'-H), 2.40 (t, J=7.5 Hz, 2H, 1"-H), 1.51 (q, J=7.5 Hz, 2H, 2"-H), 1.24 (m, 4H, 3"-H and 4"-H), 0.81 ppm (t, J=6.9 Hz, 3H, 5"-H). 13C-NMR (101 MHz, CDCl3) δ: 205.9 (1'-C), 164.6 (2-C and 6-C), 140.9 (4-C), 111.6 (1-C), 110.6 (3-C and 5-C), 35.5 (1"-C), 31.2 (3"-C), 28.7 (2"-C), 27.5 (2"-C), 22.6 (4"-C), 13.8 ppm (5"-C). HPLC-MS: [A, 15%-95%], $t_R$=9.29 min, (93%); MS (ES+) m/z=223 $[M+H]^+$.

1-[2,6-Dihydroxy-4-(1',1'-dimethylhepthyl-1-yl)phenyl]ethan-1-one

To a suspension of aluminum chloride (2.25 g; 16.95 mmol) in dichloromethane, a solution of commercially available 5-(1,1-dimethylheptyl)resorcinol (2.00 g; 8.47 mmol) in dichloromethane was added at 0° C. under a $N_2$ atmosphere and stirred for 10 min. Then, acyl chloride (1.20 mL, 16.95 mmol) was added, and the reaction was stirred at room temperature for 20 min. Afterwards, the reaction was added to a beaker containing HCl 1 N in water/ice, and the organic layer was extracted with dichloromethane, dried over $MgSO_4$ and the solvent was removed under vacuum. The crude mixture was purified by medium pressure column chromatography (dichloromethane/hexane), resulting in a yellow oil (801.4 mg, yield=34%): 1H-NMR (400 MHz, CDCl3) δ: 9.89 (bs, 2H, 2-H), 6.36 (s, 2H, 3-H), 2.72 (s, 3H, 2'-H), 1.58-1.46 (m, 2H, 2"-H), 1.31-1.12 (m, 12H, 3"-H, 4"-H, 5"-H, 8"-H), 1.13-0.95 (m, 2H, 6"-H), 0.84 (t, J=6.9 Hz, 3H, 7"-H). HPLC-MS: [A, 80%-95%], $t_R$=1.46 min, (90%); MS (ES+) m/z=279 [M+H]+.

5-Hydroxy-4H-chromen-4-one

Boron trifluoride diethyletherate (331 μL, 2.63 mmol) was added dropwise into a solution of 2',6'-dihydroxyacetophenone (100.1 mg, 0.66 mmol) N,N-dimethylformamide (1 mL) and the mixture was stirred at room temperature for 1 h. Then, a solution of methanesulfonyl chloride (152 μL, 1.98 mmol) in 0.2 mL of N,N-dimethylformamide was added to the mixture and heated at 90° C. for 3 h. Afterwards, the reaction mixture was poured into a flask containing ice/water and stirred vigorously. The crude product was filtered off and washed with water to afford a red solid. The filtrate was extracted using ethyl acetate, dried over MgSO4, and the solvent was removed under vacuum to afford a yellow crystal. Both the red solid and the yellow crystals were purified by column chromatography (4:1 hexane:ethyl acetate) giving pale yellow crystals (85.9 mg, yield=81%): 1H-NMR (400 MHz, CDCl3) δ: 12.38 (s, 1H, —OH), 7.81 (d, J=6.0 Hz, 1H, 2-H), 7.49 (t, J=8.3 Hz, 1H, 7-H), 6.86 (d, J=8.5 Hz, 1H, 6-H), 6.77 (d, J=8.3 Hz, 1H, 8-H), 6.25 (d, J=6.0 Hz, 1H, 3-H). 13C-NMR (101 MHz, CDCl3) δ: 183.107 (4-C), 160.91 (5-C), 156.79 (8a-C), 156.40 (2-C), 135.55 (7-C), 111.93 (3-C), 111.66 (6-C), 111.53 (4a-C), 107.26 (8-C). HPLC-MS: [A, 15-95%], $t_R$=5.63 min, (99%); MS (ES+) m/z=163 [M+H]+.

5-Hydroxy-7-methyl-4H-chromen-4-one

Boron trifluoride diethyletherate (318 μL, 2.53 mmol) was added dropwise into a solution of 3,5-dyhydroxy-4-acetyltoluene (105.0 mg, 0.63 mmol) N,N-dimethylformamide (1 mL) and the mixture was stirred at room temperature for 1 h. Then, a solution of methanesulfonyl chloride (146 μL, 1.90 mmol) in 0.2 mL of N,N-dimethylformamide was added to the mixture and heated at 90° C. for 3 h. Afterwards, the reaction mixture was poured into a flask containing ice/water and stirred vigorously. The crude product was filtered off and washed with water to afford a red solid. The filtrate was extracted using ethyl acetate, dried over $MgSO_4$, and the solvent was removed under vacuum to afford a yellow crystal. Both the red solid and the yellow crystals were purified by medium pressure column chromatography (4:1 hexane/ethyl acetate) giving a pale yellow solid (94.8 mg, yield=85%): 1H-NMR (400 MHz, CDCl3) δ: 12.26 (s, 1H, —OH), 7.75 (d, J=6.0 Hz, 1H, 2-H), 6.65 (s, 1H, 6-H), 6.57 (s, 1H, 8-H), 6.20 (d, J=5.9 Hz, 1H, 3-H), 2.46 (s, 3H, 1'-H). 13C-NMR (101 MHz, CDCl3) δ: 182.63 (4-C), 160.50 (5-C), 156.70 (8a-C), 156.07 (2-C), 147.45 (7-C), 112.31 (8-C), 111.49 (3-C), 109.86 (4a-C), 107.61 (6-C), 22.42 (1'-C). HPLC-MS: [A, 30-95%], $t_R$=5.09 min, (99%); MS (ES+) m/z=177 [M+H]+.

5-Hydroxy-7-pentyl-4H-chromen-4-one

Boron trifluoride diethyletherate (1.17 mL, 9.27 mmol) was added dropwise into a solution of 1-(2,6-dihydroxy-4-pentylphenyl)ethan-1-one (514.7 mg, 2.31 mmol) in N,N-dimethylformamide (4.5 mL) and the mixture was stirred at room temperature for 1 h. Then, a solution of methanesulfonyl chloride (414 μL, 5.38 mmol) in 0.5 mL of N,N-dimethylformamide was added to the mixture and heated at 90° C. for 3 h. Afterwards, the reaction mixture was poured into a flask containing ice/water and stirred vigorously. The suspension was extracted using ethyl acetate, dried over $MgSO_4$, and the solvent was removed under vacuum The resultant red oil was purified by medium pressure column chromatography (4:1 hexane:ethyl acetate) giving a yellow solid (358.2 mg, yield=67%): 1H-NMR (400 MHz, CDCl3) δ: 7.71 (d, J=6.0 Hz, 1H, 2-H), 6.64 (d, J=1.4 Hz, 1H, 8-H), 6.57 (d, J=1.4 Hz, 1H, 6-H), 6.16 (d, J=6.0 Hz, 1H, 3-H), 2.55 (t, J=7.5 Hz, 2H, 1'-H), 1.56 (q, J=7.5 Hz, 2H, 2'-H), 1.25 (m, 4H, 3'-H and 4'-H), 0.82 ppm (t, J=6.9 Hz, 3H, 5'-H). 13C-NMR (101 MHz, CDCl3) δ: 182.8 (4-C), 160.6 (5-C), 156.8 (8a-C), 156.1 (2-C), 152.5 (7-C), 111.8 (6-C), 111.6 (4a-C), 110.2 (3-C), 107.0 (8-C), 36.7 (1'-C), 31.5 (3'-C), 30.5 (2'-C), 22.6 (4'-C), 14.1 ppm (5'-C). HPLC-MS: [A, 50%-95%], $t_R$=5.90 min, (99%); MS (ES+) m/z=233 [M+H+].

5-Hydroxy-7-(1',1'-dimethylhepthyl-1-yl)-4H-chromen-4-one

70% Perchloric acid (261 μL, 4.3 mmol) was added dropwise into a solution of 1-[2,6-Dihydroxy-4-(1',1'-dimethylhepthyl-1-yl)phenyl]ethan-1-one (200.0 mg, 0.72 mmol) in triethyl orthoformate (10 mL) and the mixture was stirred at room temperature for 24 h until completion. Then, diethyl ether was added to precipitate the oxonium perchlorate salt, which was subsequently hydrolyzed in hot water. The organic layer was extracted using diethyl ether, dried over MgSO4 and the solvent removed under vacuum. The resultant dark oil was purified by medium pressure column chromatography (ethyl acetate/hexane 1:9) giving a brownish oil (110.9 mg, yield=54%): 1H-NMR (400 MHz, CDCl3) δ: 12.18 (—OH, s, 1H), 7.80 (d, J=5.9 Hz, 1H, 2-H), 6.86 (d, J=1.6 Hz, 1H, 6-H), 6.81 (d, J=1.6 Hz, 1H, 8-H), 6.25 (d, J=6.0 Hz, 1H, 3-H), 1.63-1.56 (m, 2H, 2'-H), 1.29 (s, 6H, 8'-H), 1.26-1.14 (m, 6H, 3'-H, 4'-H, 5'-H), 1.09-0.98 (m, 2H, 6'-H), 0.84 (t, J=6.9 Hz, 3H, 7'-H). 13C-NMR (101 MHz, CDCl3) δ: 182.74 (4-C), 160.25 (5-C), 159.80 (8a-C), 156.79 (7-C), 156.33 (2-C), 111.58 (5-C), 109.91 (4a-C), 109.74 (3-C), 105.05 (8-C), 44.36 (1'-C), 38.93 (2'-C), 31.85 (5'-C), 30.03 (4'-C), 28.77 (8'-C), 24.78 (3'-C), 22.76 (6'-C), 14.17 (7'-C). HPLC-MS: [A, 80%-95%], $t_R$=2.88 min, (95%); MS (ES+) m/z=289 [M+H+].

2-[1-(4-Methoxybenzyl)-1H-pyrazol-5-yl]-5-pentylbenzene-1,3-diol and 2-[1-(4-methoxybenzyl)-1H-pyrazol-3-yl]-5-pentylbenzene-1,3-diol To a warm suspension of 4-methoxybenzylhydrazine hydrochloride (1.05 g, 5.57 mmol) and sodium hydroxide (222.9 mg, 5.57 mmol) in 17 mL of ethanol was added a solution of 5-hydroxy-7-pentyl-4H-chromen-4-one (323.1 mg, 1.39 mmol) in 13 mL of ethanol. The mixture was refluxed for 4 h. After completion, the reaction was cooled down and diluted with H2O. Then, the organic layer was extracted with ethyl acetate, dried over MgSO4 and the solvent was removed under vacuum. The crude mixture was the purified by column chromatography in 3:1 to 1:1 hexane/ethyl acetate giving a pale yellow oil (272.8 mg, yield=56%) and a mixture that was then purified by column chromatography in 4:1 hexane/ethyl acetate providing a yellow oil (63.0 mg, yield=13%).

2-[1-(4-Methoxybenzyl)-1H-pyrazol-5-yl]-5-pentylbenzene-1,3-diol: 1H-NMR (300 MHz, CDCl3) δ: 7.62 (d, J=1.9 Hz, 1H, 5'-H), 6.99-6.89 (m, 2H, 2a-H), 6.72-6.64 (m, 2H, 3a-H), 6.37 (s, 2H, 3-H), 6.34 (d, J=1.9 Hz, 1H, 4'-H), 5.10 (s, 2H, —NCH2-), 3.68 (s, 3H, —OCH3), 2.60-2.44 (m, 2H, 1"-H), 1.61 (p, J=7.4 Hz, 2H, 2"-H), 1.39-1.30 (m, 4H, 3-H, 4"-H), 1.00-0.81 (m, 3H, 5"-H). 13C-NMR (75 MHz, CDCl3) δ: 159.15 (4a-C), 154.89 (1-C), 147.43 (5-C), 139.78 (5'-C), 133.76 (3'-C), 129.44 (2a-C), 128.77 (1a-C), 113.96 (3a-C), 108.11 (4'-C), 107.82 (3-C), 102.09 (2-C), 55.24 (—OCH3), 53.31 (—NCH2), 36.03 (1"-C), 31.56 (3-C), 30.74 (2"-C), 22.66 (4"-C), 14.17 (5"-C). HPLC-MS: [A, 40-95%], $t_R$=5.17 min, (99%); MS (ES+) m/z=367 [M+H]+.

2-[1-(4-Methoxybenzyl)-1H-pyrazol-3-yl]-5-pentylbenzene-1,3-diol: 1H-NMR (300 MHz, CDCl3) δ: 8.63 (bs, 2H, —OH), 7.27 (d, J=2.4 Hz, 1H, 5'-H), 7.12-7.05 (m, 2H, 3a-H), 6.91 (d, J=2.4 Hz, 1H, 4'-H), 6.79-6.72 (m, 2H, 2a-H), 6.24 (s, 2H, 3-H), 5.13 (s, 2H, —NCH2-), 3.67 (s, 3H, —OCH3), 2.43-2.30 (m, 2H, 1"-H), 1.55-1.38 (m, 2H, 2"-H), 1.27-1.11 (m, 4H, 3-H, 4"-H), 0.84-0.73 (m, 3H, 5"-H). 13C-NMR (75 MHz, CDCl3) δ: 159.58 (4a-C), 155.71 (1-C), 148.60 (3'-C), 144.45 (5-C), 129.49 (1a-C), 129.44 (3a-C), 128.03 (5'-C), 114.35 (2a-C), 108.31 (3-C), 107.01 (4'-C), 103.33 (2-C), 55.52 (—NCH2-), 55.39 (—OCH3), 35.74 (1"-C), 31.55 (3-C), 30.67 (2"-C), 22.64 (4"-C), 14.13 (5"-C). HPLC-MS: [A, 50-95%], $t_R$=6.88 min, (90%); MS (ES+) m/z=367 [M+H]+.

2-[1-(3-Methoxybenzyl)-1H-pyrazol-5-yl]-5-pentylbenzene-1,3-diol and 2-[1-(3-methoxybenzyl)-1H-pyrazol-3-yl]-5-pentylbenzene-1,3-diol A suspension of 3-methoxybenzylhydrazine dihydrochloride (709.9 mg, 3.16 mmol) in 7 mL of ethanol was neutralized with sodium hydroxide (252.4 mg, 6.31 mmol). Then, a solution of 3c in 4 mL of ethanol was added (183.0 mg, 0.79 mmol) and the mixture was refluxed for 4 h. After completion, the reaction was cooled down and diluted with H2O. Then, the organic layer was extracted with ethyl acetate, dried over MgSO4 and the solvent was removed under vacuum. The crude mixture was the purified by medium pressure column chromatography in 20 to 60% ethyl acetate in hexane giving a brown/yellow oil (35.8 mg, yield=11%) and a yellowish oil (163.0 mg, yield=56%).

2-[1-(3-Methoxybenzyl)-1H-pyrazol-5-yl]-5-pentylbenzene-1,3-diol: 1H-NMR (300 MHz, CDCl3) δ: 7.64 (d, J=1.9 Hz, 1H, 5'-H), 7.07 (dd, J=8.3, 7.5 Hz, 1H, ar), 6.70 (ddd, J=8.3, 2.6, 1.0 Hz, ar), 6.60 (dt, J=7.5, 1.3 Hz, 1H, ar), 6.52 (dd, 1H, J=2.6, 1.6 Hz, ar), 6.41-6.31 (m, 3H, 4'-H, 3-H), 5.14 (s, 2H, —NCH2-), 2.54-2.40 (m, 2H, 1"-H), 1.58 (p, J=7.5 Hz, 2H, 2"-H), 1.39-1.25 (m, 4H, 3-H, 4"-H), 0.94-0.86 (m, 3H, 5"-H). 13C-NMR (75 MHz, CDCl3) δ: 159.70 (2a-C), 154.90 (1-C), 147.46 (5-C), 139.89 (5'-C), 138.14 (1a-C), 134.11 (3'-C), 129.63, 120.25, 113.95 and 112.99 (ar-C), 108.11 (4'-C), 107.77 (3-C), 102.02 (2-C), 55.09 (—OCH3), 53.82 (—NCH2), 36.03 (1"-C), 31.59 (3-C), 30.73 (2"-C), 22.66 (4"-C), 14.16 (5"-C). HPLC-MS: [A, 50-95%], $t_R$=2.35 min, (88%); MS (ES+) m/z=367 [M+H]+.

2-[1-(3-Methoxybenzyl)-1H-pyrazol-3-yl]-5-pentylbenzene-1,3-diol: 1H-NMR (300 MHz, CDCl3) δ: 8.86 (bs, 2H, OH), 7.41 (d, J=2.4 Hz, 1H, 5'-H), 7.30-7.19 (m, 1H, ar), 7.07 (d, J=2.4 Hz, 1H, 4'-H), 6.89-6.74 (m, 3H, ar), 6.36 (s, 2H, 3-H), 5.27 (s, 2H, —NCH2), 3.76 (s, 3H, —OCH3), 2.53-2.40 (m, 2H, 1"-H), 1.57 (p, J=7.3 Hz, 2H, 2"-H), 1.37-1.24 (m, 4H, 3-H, 4"-H), 0.93-0.84 (m, 3H, 5"-H). 13C-NMR (75 MHz, CDCl3) δ: 159.94 (2a-C), 155.77 (1-C), 148.76 (3'-C), 144.43 (5-C), 137.56 (1a-C), 130.00 (ar), 129.78 (5'-C), 120.05, 113.72 and 113.34 (ar-C), 108.24 (3-C), 107.23 (4'-C), 103.26 (2-C), 55.85 (—NCH2), 55.30 (—OCH3), 35.72 (1"-C), 31.53 (3"-C), 30.64 (2"-C), 22.61 (4"-C), 14.11 (5"-C). HPLC-MS: [A, 50-95%], $t_R$=6.99 min, (99%); MS (ES+) m/z=367 [M+H]+.

Example 2. 2-(1-Isopropyl-1H-pyrazol-5-yl)benzene-1,3-diol and 2-(1-isopropyl-1H-pyrazol-3-yl)benzene-1,3-diol Isopropyl hydrazine hydrochloride (424 mg, 3.53 mmol) and NaOH pellets (153 mg, 3.53 mmol) were suspended in 15 mL of ethanol and heated to reflux temperature. To this mixture, 5-hydroxy-4H-chromen-4-one (155 mg, 0.96 mmol) was incorporated and the reaction was refluxed for 2.5 h. Then, the mixture was cooled down, dissolved with H₂O and the organic layers were extracted with ethyl acetate. The combined organic layers were dried over MgSO4 and the solvent removed under vacuum. The resultant yellow oil was purified by medium pressure column chromatography using 0 to 30% of ethyl acetate in dichloromethane, giving a pale-yellow solid (127.4 mg, yield=61%; 2-(1-Isopropyl-1H-pyrazol-5-yl)benzene-1,3-diol) and another pale-yellow solid (15.7 mg, yield=8%; 2-(1-isopropyl-1H-pyrazol-3-yl)benzene-1,3-diol).

2-(1-Isopropyl-1H-pyrazol-5-yl)benzene-1,3-diol:
1H-NMR (400 MHz, DMSO-d6) δ: 7.45 (d, J=1.9 Hz, 1H, 5'-H), 7.02 (t, J=8.2 Hz, 1H, 5-H), 6.41 (dd, J=8.2 Hz, J=1.7 Hz, 2H, 3-H), 6.05 (d, J=1.9 Hz, 1H, 4'-H), 4.14 (m, 1H, CH), 1.31 (d, J=6.6 Hz, 6H, CH(CH3)2). 13C-NMR (101 MHz, DMSO-d6) δ: 157.16 (1-C), 137.77 (5'-C), 135.26 (5-C), 130.35 (3'-C), 106.59 (3-C), 106.51 (4'-C), 105.63 (2-C), 49.92 (CH), 22.74 (CH(CH3)2). HPLC-MS: [A, 15-95%], $t_R$=2.42 min, (97%); MS (ES+) m/z=219 [M+H]⁺. Anal. calcd. for C12H14N2O2: C: 66.04%; H: 6.47%, N: 12.84%, found: C: 49.57%; H: 8.02%; N: 7.02%; S: 16.1%.

2-(1-Isopropyl-1H-pyrazol-3-yl)benzene-1,3-diol:
1H-NMR (400 MHz, CD3OD) δ: 7.69 (d, J=2.5 Hz, 1H, 5'-H), 7.13 (d, J=2.5 Hz, 1H, 4'-H), 6.99 (t, J=8.1 Hz, 1H, 5-H), 6.46 (d, J=8.1 Hz, 2H, 3-H), 4.62 (hept, J=8.1 Hz, 1H, CH), 1.58 (d, J=6.7 Hz, 6H, CH(CH3)2). 13C-NMR (101 MHz, CD3OD) δ: 157.90 (1-C), 149.56 (3'-C), 129.17 (5-C), 128.26 (5'-C), 108.04 (3-C), 107.71 (4'-C), 106.76 (2-C), 54.70 (CH), 22.97 (CH(CH3)2). HPLC-MS: [A, 15-95%], $t_R$=7.45 min, (97%); MS (ES+) m/z=219 [M+H]⁺.

Example 3. 2-(1-Ethyl-1H-pyrazol-5-yl)-5-methylbenzene-1,3-diol and 2-(1-ethyl-1H-pyrazol-3-yl)-5-methylbenzene-1,3-diol Ethylhydrazine oxalate (409.1 mg, 2.73 mmol) and NaOH pellets (218.2 mg, 5.45 mmol) were suspended in 10 mL of ethanol and heated to reflux temperature. To this mixture, 5-hydroxy-7-methyl-4H-chromen-4-one (120.0 mg, 0.68 mmol) was incorporated and the reaction was refluxed for 1.5 h. Then, the mixture was cooled down, dissolved with H₂O and the organic layers were extracted with ethyl acetate. The combined organic layers were dried over MgSO₄ and the solvent removed under vacuum. The resultant yellow solid was purified twice by medium pressure column chromatography using 30% of ethyl acetate in hexane, giving a pale white solid (103.3 mg, yield=70%; 2-(1-Ethyl-1H-pyrazol-5-yl)-5-methylbenzene-1,3-diol) and a yellow solid (5.0 mg, yield=3%; 2-(1-ethyl-1H-pyrazol-3-yl)-5-methylbenzene-1,3-diol)

2-(1-Ethyl-1H-pyrazol-5-yl)-5-methylbenzene-1,3-diol:
1H-NMR (400 MHz, CD₃OD) δ: 7.48 (d, J=1.9 Hz, 1H, 5'-H), 6.25 (s, 2H, 3-H), 6.15 (d, J=1.9 Hz, 1H, 4'-H), 3.93 (q, J=7.3 Hz, 2H, CH2), 2.20 (s, 3H, 6-H), 1.27 (t, J=7.3 Hz, 3H, CH3). 13C-NMR (101 MHz, CD3OD) δ: 157.57 (1-C), 142.22 (5-C), 138.98 (5'-C), 137.51 (3'-C), 108.51 (3-C), 108.36 (4'-C), 103.61 (2-C), 45.28 (CH2), 21.63 (6-C), 15.61 (CH3). HPLC-MS: [A, 15-95%], $t_R$=3.23 min, (99%); MS (ES+) m/z=219 [M+H]⁺. Anal. calcd. for C12H14N2O2: C: 66.04%; H: 6.47%, N: 12.84%, found: C: 65.70%; H: 6.66%; N: 12.58%.

2-(1-Ethyl-1H-pyrazol-3-yl)-5-methylbenzene-1,3-diol:
1H-NMR (400 MHz, CDCl3) δ: 8.40 (s, 2H, OH), 7.44 (d, J=2.4 Hz, 1H, 5'-H), 6.96 (d, J=2.4 Hz, 1H, 4'-H), 6.33 (s, 2H, 3-H), 4.21 (q, J=7.3 Hz, 2H, CH2), 2.25 (s, 3H, 6-H), 1.52 (t, J=7.3 Hz, 3H, CH3). 13C-NMR (101 MHz, CDCl3) δ: 155.73 (1-C), 148.15 (3'-C), 139.22 (5-C), 128.89 (5'-C), 109.02 (3-C), 106.32 (4'-C), 103.22 (2-C), 47.05 (CH2), 21.41 (6-C), 15.41 (CH3). HPLC-MS: [A, 15-95%], $t_R$=7.48 min, (96%); MS (ES+) m/z=219 [M+H]⁺.

Example 4.
5-Methyl-2-(1H-pyrazol-3-yl)benzene-1,3-diol

Hydrazine monohydrate (105 μL, 2.17 mmol) was added to a stirring solution of 5-hydroxy-7-methyl-4H-chromen-4-one (95.4 mg, 0.54 mmol) in ethanol (7 mL), and the reaction was refluxed for 40 min. Then, the reaction was cooled and diluted with H₂O, and the organic layer was extracted using ethyl acetate, dried over MgSO₄ and the solvent removed under vacuum. The crude mixture was purified by column chromatography (EtOAc/hexane, 1:2), resulting in a white solid (98.8 mg, yield=96%).

1H-NMR (400 MHz, CD3OD) δ: 7.63 (d, J=2.4 Hz, 1H, 5'-H), 7.08 (d, J=2.4 Hz, 1H, 4'-H), 6.28 (s, 2H, 3-H), 4.87 (s, 2H, OH), 2.20 (s, 3H, 6-H); 13C-NMR (101 MHz, CD3OD) δ: 157.62 (1-C), 148.68 (3'-C), 139.85 (5-C), 130.32 (5'-C), 108.90 (3-C), 106.89 (4'-C), 104.06 (2-C), 21.39 (6-C). HPLC-MS: [A, 15%-95%], $t_R$=3.84 min (99%); MS (ES+) m/z=191 [M+H+]. Anal. calcd. for C10H10N2O2: C: 63.15%; H: 5.30%, N: 14.73%, found: C: 62.38%; H: 5.58%; N: 14.21%.

Example 5. 2-(1-Isopropyl-1H-pyrazol-5-yl)-5-methylbenzene-1,3-diol and 2-(1-isopropyl-1H-pyrazol-3-yl)-5-methylbenzene-1,3-diol Isopropyl hydrazine hydrochloride (445.0 mg, 4.01 mmol) and NaOH pellets (160.4 mg, 4.01 mmol) were suspended in 25 mL of ethanol and heated to reflux temperature. To this mixture, 5-hydroxy-7-methyl-4H-chromen-4-one (176.4 mg, 1.00 mmol) was incorporated and the reaction was refluxed for 2.5 h. Then, the mixture was cooled down, dissolved with H₂O and the organic layers were extracted with ethyl acetate. The combined organic layers were dried over MgSO₄ and the solvent removed under vacuum. The resultant yellow solid was purified twice by medium pressure column chromatography. First using 0 to 30% of ethyl acetate in dichloromethane, secondly in 50 to 70% ethyl acetate in hexane, giving a pale-yellow solid (141.8 mg, yield=61%; 2-(1-Isopropyl-1H-pyrazol-5-yl)-5-methylbenzene-1,3-diol) and a white solid (13.9 mg, yield=6%; 2-(1-isopropyl-1H-pyrazol-3-yl)-5-methylbenzene-1,3-diol)

2-(1-Isopropyl-1H-pyrazol-5-yl)-5-methylbenzene-1,3-diol: 1H-NMR (400 MHz, CD3OD) δ: 7.53 (d, J=1.9 Hz, 1H, 5'-H), 6.27 (s, 2H, 3-H), 6.15 (d, J=1.9 Hz, 1H, 4'-H), 4.27 (hept, J=6.7 Hz, 1H, CH), 2.22 (s, 3H, 6-H), 1.38 (d, J=6.7 Hz, 6H, CH(CH3)2). 13C-NMR (101 MHz, CD3OD) δ: 157.67 (1-C), 142.11 (5-C), 139.12 (5'-C), 136.96 (3'-C), 108.46 (3-C), 107.74 (4'-C), 103.71 (2-C), 51.40 (CH), 22.74 (CH(CH3)2), 21.62 (6-C). HPLC-MS: [A, 15-95%], $t_R$=4.47 min, (95%); MS (ES+) m/z=233 [M+H]⁺.

2-(1-Isopropyl-1H-pyrazol-3-yl)-5-methylbenzene-1,3-diol: 1H-NMR (400 MHz, CD3OD) δ: 7.65 (d, J=2.5 Hz, 1H, 5'-H), 7.04 (d, J=2.5 Hz, 1H, 4'-H), 6.28 (s, 2H, 3-H), 4.58 (hept, J=6.7 Hz, 1H, CH), 2.24 (s, 3H, 6-H), 1.55 (d, J=6.7 Hz, 6H, CH(CH3)2). 13C-NMR (101 MHz, CD3OD) δ: 157.78 (1-C), 149.82 (3'-C), 139.64 (5-C), 128.30 (5'-C), 108.87 (3-C), 107.36 (4'-C), 104.29 (2-C), 54.71 (CH), 22.98 (CH(CH3)2), 21.42 (6-C). HPLC-MS: [A, 15-95%], $t_R$=8.01 min, (97%); MS (ES+) m/z=233 [M+H]⁺.

Example 6. 2-(1-Cyclohexyl-1H-pyrazol-3-yl)-5-methylbenzene-1,3-diol and 2-(1-cyclohexyl-1H-pyrazol-5-yl)-5-methylbenzene-1,3-diol A solution of, 5-hydroxy-7-methyl-4H-chromen-4-one (120.0 mg; 0.68 mmol) in 5 mL of ethanol was added to a stirring suspension of cyclohexylhydrazine hydrochloride (409.1 mg; 2.73 mmol) with sodium hydroxide (109.1 mg; 2.73 mmol) in 5 mL of ethanol and the mixture was refluxed for 1 h. Then, the reaction was cooled down and diluted in H$_2$O. The organic layer was extracted with ethyl acetate, dried over MgSO4 and the solvent was removed under vacuum. The resultant yellow oil was purified by column chromatography in hexane/ethyl acetate (from 3:1 to 2:1) to provide a light yellow oil (153.6 mg; yield=83%; 2-(1-Cyclohexyl-1H-pyrazol-3-yl)-5-methylbenzene-1,3-diol) and another yellow solid (24.1 mg, yield=12%; 2-(1-cyclohexyl-1H-pyrazol-5-yl)-5-methylbenzene-1,3-diol).

2-(1-Cyclohexyl-1H-pyrazol-3-yl)-5-methylbenzene-1,3-diol. 1H-NMR (400 MHz, CDCl3) δ: 7.66 (d, J=1.9 Hz, 1H, 5'-H), 6.97 (s, 2H, —OH), 6.41 (s, 2H, 3-H), 6.28 (d, J=1.9 Hz, 1H, 4'-H), 3.91 (tt, J=10.4, 5.2 Hz, 1H, 1Cy-H), 2.26 (s, 3H, 6-H), [1.96-1.83 (m, 4H), 1.81-1.50 (m, 4H), 2Cy-H, 3Cy-H], 1.23-1.05 (m, 2H, 4Cy-H). 13C-NMR (101 MHz, CDCl3) δ: 155.28 (1-C), 141.84 (5-C), 139.16 (5'-C), 133.32 (3'-C), 108.28 (3-C), 106.87 (4'-C), 102.02 (2-C), 58.61 (1Cy-C), 32.92, 25.70 (2Cy-C, 3Cy-C), 25.15 (4Cy-C), 21.63 (6-C). HPLC-MS: [A, 15-95%], t$_R$=6.21 min, (99%); MS (ES+) m/z=273 [M+H]$^+$.

2-(1-Cyclohexyl-1H-pyrazol-5-yl)-5-methylbenzene-1,3-diol. 1H-NMR (400 MHz, CD3OD) δ: 7.65 (d, J=2.4 Hz, 1H, 5'-H), 7.03 (d, J=2.4 Hz, 1H, 4'-H), 6.27 (s, 2H, 3-H), 4.19 (tt, J=11.4, 3.8 Hz, 1H, 1Cy-H), 2.22 (s, 3H, 6-H), [1.98-1.87 (m, 2H), 1.81-1.50 (m, 2H), 3Cy-H], 1.88-1.71 (m, 4H, 2Cy-H), 1.42-1.28 (m, 2H, 4Cy-H). 13C-NMR (101 MHz, CD3OD) δ: 157.78 (1-C), 149.63 (3'-C), 139.62 (5-C), 128.44 (5'-C), 108.87 (3-C), 107.26 (4'-C), 104.29 (2-C), 62.01 (1Cy-C), 34.42 (2-Cy-C), 26.49 (4Cy-C), 26.35 (3Cy-C), 21.44 (6-C). HPLC-MS: [A, 15-95%], t$_R$=9.26 min, (92%); MS (ES+) m/z=273 [M+H]$^+$. Anal. calcd. for C16H20N2O2: C: 70.56%; H: 7.40%, N: 10.29%, found: C: 67.70%; H: 7.39%; N: 9.55%.

Example 7. 2-(1-Benzyl-1H-pyrazol-5-yl)-5-methylbenzene-1,3-diol and 2-(1-benzyl-1H-pyrazol-3-yl)-5-methylbenzene-1,3-diol To a suspension of benzylhydrazine dihydrochloride (261.5 mg, 1.34 mmol) and sodium hydroxide pellets (107.0 mg, 2.68 mmol) in 10 mL of ethanol, a solution of 5-hydroxy-7-methyl-4H-chromen-4-one (59.0 mg, 0.34 mmol) in 10 mL of ethanol was added and the mixture was refluxed overnight. Then, the mixture was cooled down, dissolved in water and extracted with ethyl acetate. The combined organic layers were dried over MgSO$_4$, filtered and the solvent removed under vacuum. The resultant yellow oil was purified by medium pressure column chromatography using 20 to 50% ethyl acetate in hexane, giving a yellow oil (21.0 mg, yield=22%; 2-(1-Benzyl-1H-pyrazol-5-yl)-5-methylbenzene-1,3-diol) and a yellow oil (31.3 mg, yield=33%; 2-(1-benzyl-1H-pyrazol-3-yl)-5-methylbenzene-1,3-diol).

2-(1-Benzyl-1H-pyrazol-5-yl)-5-methylbenzene-1,3-diol. 1H-NMR (400 MHz, CDCl3) δ: 7.66 (d, J=1.9 Hz, 1H, 5'-H), 7.21-7.13 (m, 3H, 3a-H, 4a-H), 7.04-6.95 (m, 2H, 2a-H), 6.36 (d, J=1.9 Hz, 1H, 4'-H), 6.34 (s, 2H, 3-H), 6.33-5.86 (bs, 2H, —OH), 5.15 (s, 2H, CH2), 2.25 (s, 3H, 6-H). 13C-NMR (101 MHz, CDCl3) δ: 0.154.83 (1-C), 142.39 (5-C), 140.01 (5'-C), 136.65 (1a-C), 133.87 (3'-C), 128.64, 127.90 and 127.84 (2a-C, 3a-C, 4a-C), 108.55 (3-C), 108.20 (4'-C), 101.81 (2-C), 53.80 (CH), 21.73 (6-C). HPLC-MS: [A, 15-95%], t$_R$=6.06 min, (99%); MS (ES+) m/z=261 [M+H]$^+$. Anal. calcd. for C17H16N2O2: C: 72.84%; H: 5.75%, N: 9.99%, found: C: 64.67%; H: 6.19%; N: 7.90%.

2-(1-Benzyl-1H-pyrazol-3-yl)-5-methylbenzene-1,3-diol. 1H-NMR (400 MHz, MD3OD) δ: 7.60 (d, J=2.4 Hz, 1H, 5'-H), 7.35-7.20 (m, 5H, 2a-H, 3a-H, 4a-H), 7.06 (d, J=2.4 Hz, 1H, 4'-H), 6.24 (d, J=0.8 Hz, 2H, CH2), 5.30 (s, 2H, 3-H), 2.19 (s, 3H, 6-H). 13C-NMR (101 MHz, MD3OD) δ: 0.157.77 (1-C), 150.60 (3'-C), 139.90 (5'-C), 138.13 (1a-C), 130.99 (5'-C), 129.72, 128.96, 128.74, (2a-C, 3a-C, 4a-C), 108.90 (3-C), 108.13 (4'-C), 104.10 (2-C), 56.42 (CH), 21.43 (6-C). HPLC-MS: [A, 15-95%], t$_R$=8.58 min, (99%); MS (ES+) m/z=261 [M+H]$^+$. Anal. calcd. for C17H16N2O2: C: 72.84%; H: 5.75%, N: 9.99%, found: C: 72.53%; H: 5.99%; N: 9.53%.

Example 8. 5-Methyl-2-(1-(pyridin-4-ylmethyl)-1H-pyrazol-5-yl)benzene-1,3-diol

To a stirring suspension of (4-pyridyl)methyl hydrazine dihydrochloride (334.4 mg; 1.70 mmol) and sodium hydroxide (136.4 mg; 3.41 mmol) in 10 mL of ethanol, a solution of 5-hydroxy-7-methyl-4H-chromen-4-one (100.0 mg; 0.57 mmol) in 5 mL of ethanol was added and the mixture was stirred under reflux overnight. After that time, the reaction mixture was cooled down, dissolved in H2O, and the organic layer was extracted with EtOAc. The organic layer was dried over MgSO4, filtered, and the solvent was removed under vacuum. The crude oil was purified by medium pressure column chromatography in 75%-100% ethyl acetate in hexane and then 0%-10% acetonitrile in ethyl acetate to provide 99.4 mg of a yellow solid 4f (yield=66%). 1H-NMR (400 MHz, DMSO-d6) δ: 9.42 (s, 2H, —OH), 8.41 (d, J=5.7 Hz, 2H, 3a-H), 7.51 (d, J=1.8 Hz, 1H, 5'-H), 6.99 (d, J=5.8 Hz, 2H, 2a-H), 6.22 (s, 2H, 3-H), 6.19 (d, J=1.8 Hz, 1H, 4'-H), 5.13 (s, 2H, CH2), 2.14 (s, 3H, 6-H). 13C-NMR (101 MHz, DMSO-d6) δ: 156.42 (1-C), 149.26 (3a-C), 147.12 (1a-C), 139.98 (5-C), 138.59 (5'-C), 137.15 (3'-C), 122.03 (2a-C), 107.50 (4'-C), 107.16 (3-C), 101.97 (2-C), 51.36 (CH2), 21.24 (6-C). HPLC-MS: [A, 2-50%], t$_R$=2.67 min, (99%); MS (ES+) m/z=282 [M+H]$^+$.

Example 9. 2-(1-Methyl-1H-pyrazol-5-yl)-5-pentylbenzene-1,3-diol

Methylhydrazine (181 μL, 3.45 mmol) was added to a solution of 5-hydroxy-7-pentyl-4H-chromen-4-one (200.0 mg, 0.86 mmol) in 15 mL of EtOH and the reaction was refluxed for 6 h. Then, the mixture was cooled down and diluted in H$_2$O. The organic layer was extracted with CH$_2$Cl$_2$, dried over MgSO$_4$ and the solvent was removed under vacuum. Afterwards, the resultant yellow oil was purified by medium pressure column chromatography (ethyl acetate/hexane, 1:1) giving a brown solid (72.7 mg, yield=32%): 1H-NMR (400 MHz, CDCl3) δ: 7.59 (d, J=1.9 Hz, 1H, 5'-H), 6.63 (bs, 2H, —OH), 6.42 (s, 2H, 3-H), 6.36 (d, J=1.9 Hz, 1H, 4'-H), 3.73 (s, 3H, —NCH3), 2.53 (t, J=7.2 Hz, 2H, 1''-H), 1.62 (p, J=7.2 Hz, 2H, 2''-H), 1.38-1.30 (m, 4H, 3-H, 4''-H), 0.90 (t, J=6.9 Hz, 1H, 5''-H). 13C-NMR (101 MHz, CDCl3) δ: 154.98 (1-C), 147.45 (3'-C), 139.11 (5-C), 134.54 (5'-C), 107.85 (3-C), 107.46 (2-C), 101.91 (4'-C), 37.04 (—NCH3), 36.11 (1''-C), 31.66 (3-C), 30.77 (2''-C), 22.69 (4''-C), 14.19 (5''-C). HPLC-MS: [A, 15-95%], t$_R$=5.71 min, (95%); MS (ES+) m/z=261 [M+H]$^+$.

Example 10. 2-(1-Ethyl-1H-pyrazol-5-yl)-5-pentylbenzene-1,3-diol and 2-(1-ethyl-1H-pyrazol-3-yl)-5-pentylbenzene-1,3-diol A 5 mL solution of 5-hydroxy-7-pentyl-4H-chromen-4-one (148.0 mg; 0.64 mmol) in ethanol was incorporated to a stirring suspension of ethylhydrazine oxalate (382.8 mg; 2.55 mmol) and sodium hydroxide (204.1 mg; 5.10 mmol) in 10 mL of ethanol. The mixture was stirred for 2.5 h, and then cooled down to rt and dissolved with $H_2O$. The organic layer was extracted with EtOAc, dried over $MgSO_4$, filtered, and the solvent was removed under vacuum. The resultant yellow oil was purified by medium pressure column chromatography (30-50% ethyl acetate in hexane) to provide 118.7 mg of a brown solid (yield=62%; 2-(1-Ethyl-1H-pyrazol-5-yl)-5-pentylbenzene-1,3-diol) and 16.3 mg of a brown oil (yield=8%; 2-(1-ethyl-1H-pyrazol-3-yl)-5-pentylbenzene-1,3-diol).

2-(1-Ethyl-1H-pyrazol-5-yl)-5-pentylbenzene-1,3-diol: 1H-NMR (400 MHz, CDCl3) δ: 7.62 (d, J=2.0 Hz, 1H, 5'-H), 7.14 (s, 2H, —OH), 6.43 (s, 2H, 3-H), 6.33 (d, J=2.0 Hz, 1H, 4'-H), 4.03 (q, J=7.2 Hz, 2H, CH2), 2.56-2.48 (m, 2H, 1"-H), 1.61 (p, J=7.3 Hz, 2H, 2"-H), 1.40-1.26 (m, 7H, 3"-H, 4"-H, CH3), 0.95-0.84 (m, 3H, 5"-H). 13C-NMR (101 MHz, CDCl3) δ: 155.22 (1-C), 147.21 (5-C), 139.12 (5'-C), 134.08 (3'-C), 107.63 (3-C), 107.43 (4'-C), 101.99 (2-C), 44.75 (—CH2-), 36.04 (1"-C), 31.58 (3"-C), 30.70 (2"-C), 22.61 (4"-C), 15.40 (—CH3), 14.10 (5"-C). HPLC-MS: [A, 15-95%], $t_R$=7.33 min, (92%); MS (ES+) m/z=275 $[M+H]^+$.

2-(1-Ethyl-1H-pyrazol-3-yl)-5-pentylbenzene-1,3-diol: 1H-NMR (400 MHz, CDCl3) δ: 8.42 (bs, 2H, —OH), 7.43 (d, J=2.4 Hz, 1H, 5'-H), 6.96 (d, J=2.4 Hz, 1H, 4'-H), 6.34 (s, 2H, 3-H), 4.21 (q, J=7.3 Hz, 2H, CH2), 2.52-2.44 (m, 2H, 1"-H), 1.65-1.54 (m, 2H, 2"-H), 1.52 (t, J=7.3 Hz, 3H, CH3), 1.37-1.25 (m, 4H, 3-H, 4"-H), 0.88 (t, J=7.0 Hz, 3H, 5"-H). 13C-NMR (101 MHz, CDCl3) δ: 155.69 (1-C), 148.19 (2-C), 144.35 (3'-C), 128.88 (5'-C), 108.34 (3-C), 106.32 (4'-C), 103.42 (5-C), 47.05 (CH2), 35.71 (1"-C), 31.60, (3-C), 30.71 (2"-C), 22.69 (4"-C), 15.41 (—CH3), 14.17 (5"-C). HPLC-MS: [A, 15-95%], $t_R$=9.68 min, (90%); MS (ES+) m/z=275 $[M+H]^+$.

Example 11. 2-(1-Isopropyl-1H-pyrazol-5-yl)-5-pentylbenzene-1,3-diol and 2-(1-isopropyl-1H-pyrazol-3-yl)-5-pentylbenzene-1,3-diol Isopropyl hydrazine hydrochloride (245 mg, 2.21 mmol) and NaOH pellets (88.3 mg, 2.21 mmol) were suspended in 15 mL of ethanol and heated to reflux temperature. To this mixture, 5-hydroxy-7-pentyl-4H-chromen-4-one (128 mg, 0.55 mmol) was incorporated and the reaction was refluxed for 3 h. Then, the mixture was cooled down and filtered and the solvent was removed under vacuum. The crude mixture was then purified by medium pressure column chromatography using 20 to 50% of ethyl acetate in hexane, giving a yellow solid (80.9 mg, yield=51%; 2-(1-Isopropyl-1H-pyrazol-5-yl)-5-pentylbenzene-1,3-diol) and another yellow solid (11.0 mg, yield=7%; 2-(1-isopropyl-1H-pyrazol-3-yl)-5-pentylbenzene-1,3-diol). 2-(1-Isopropyl-1H-pyrazol-5-yl)-5-pentylbenzene-1,3-diol: 1H-NMR (400 MHz, CDCl3) δ: 7.73 (d, J=1.8 Hz, 1H, 5'-H), 6.42 (s, 2H, 3-H), 6.33 (d, J=1.8 Hz, 1H, 4'-H), 5.39 (s, 2H, —OH), 4.29 (hept, J=6.6 Hz, 1H, CH), 2.54 (t, J=7.6 Hz, 2H, 1"-H), 1.63 (p, J=7.4 Hz, 2H, 2"-H), 1.42 (d, J=6.6 Hz, 6H, CH(CH3)2), 1.37-1.31 (m, 4H, 3-H, 4"-H), 0.90 (t, J=4.2 Hz, 3H). 13C-NMR (101 MHz, CDCl3) δ: 154.65 (1-C), 147.50 (3'-C), 140.00 (5'-C), 131.45 (5-C), 107.83 (3-C), 107.47 (4'-C), 102.02 (2-C), 50.98 (—CH—), 36.12 (1"-C), 31.66 (3-C), 30.72 (2"-C), 22.85 (CH(CH3)2), 22.68 (3-C), 14.16 (5"-C). HPLC-MS: [A, 30-95%], $t_R$=6.18 min, (98%); MS (ES+) m/z=289 $[M+H]^+$. Anal. calcd. for C17H24N2O2: C: 70.80%; H: 8.39%, N: 9.71%, found: C: 70.82%; H: 8.50%; N: 9.35%.

2-(1-Isopropyl-1H-pyrazol-3-yl)-5-pentylbenzene-1,3-diol: 1H-NMR (400 MHz, CDCl3) δ: 8.47 (bs, 2H, —OH), 7.46 (d, J=2.5 Hz, 1H, 5'-H), 6.95 (d, J=2.5 Hz, 1H, 4'-H), 6.33 (s, 2H, 3-H), 4.52 (hept, J=6.7 Hz, 1H, CH), 2.49 (t, J=7.7 Hz, 2H, 1"-H), 1.65-1.56 (m, 2H, 2"-H), 1.54 (d, J=6.6 Hz, 6H, CH(CH3)2), 1.34-1.29 (m, 4H, 3-H, 4"-H), 0.88 (t, J=6.7 Hz, 3H, 5"-H). 13C-NMR (101 MHz, CDCl3) δ: 155.71 (1-C), 147.82 (2-C), 144.29 (5-C), 127.11 (5'-C), 108.30 (3-C), 105.97 (4'-C), 103.51 (2-C), 53.84 (CH), 35.80 (1"-C), 31.59, 22.70 (3-C, 4"-C), 30.74 (2"-C), 22.86 (CH(CH3)2), 14.17 (5"-C). HPLC-MS: [A, 30-95%], $t_R$=9.32 min, (96%); MS (ES+) m/z=289 $[M+H]^+$.

Example 12. 2-(1-(Tert-butyl)-1H-pyrazol-5-yl)-5-pentylbenzene-1,3-diol and 2-(1-(tert-butyl)-1H-pyrazol-3-yl)-5-pentylbenzene-1,3-diol To a stirring suspension of tert-butylhydrazine hydrochloride (171.9 mg; 1.38 mmol) and sodium hydroxide (55.2 mg; 1.38 mmol) in 7 mL of ethanol, a solution of 5-hydroxy-7-pentyl-4H-chromen-4-one (80.0 mg; 0.34 mmol) in 3 mL of ethanol was incorporated and the mixture was refluxed for 8 h. Then, the mixture was cooled down and diluted with $H_2O$. The organic layer was extracted using EtOAc, dried over $MgSO_4$, and the solvent was removed under vacuum. Afterwards, the crude mixture was purified by medium pressure column chromatography (20-80% ethyl acetate in hexane) to give a yellow oil (28.5 mg; yield=27%; 2-(1-(Tert-butyl)-1H-pyrazol-5-yl)-5-pentylbenzene-1,3-diol) and another yellow oil (4.8 mg; yield=5%; and 2-(1-(tert-butyl)-1H-pyrazol-3-yl)-5-pentylbenzene-1,3-diol).

2-[1-(Tert-butyl)-1H-pyrazol-5-yl]-5-pentylbenzene-1,3-diol: 1H-NMR (400 MHz, CDCl3) δ: 7.64 (d, J=1.7 Hz, 1H, 5'-H), 6.39 (s, 2H, 3-H), 6.30 (d, J=1.7 Hz, 1H, 4'-H), 5.01 (s, 2H, —OH), 2.58-2.49 (m, 2H, 1"-H), 1.62 (p, J=7.5 Hz, 2H, 2"-H), 1.51 (s, 9H, —C(CH3)3), 1.38-1.28 (m, 4H, 3-H, 4"-H), 0.94-0.84 (m, 3H, 5"-H). 13C-NMR (101 MHz, CDCl3) δ: 154.49 (1-C), 147.40 (5-C), 138.46 (5'-C), 130.69 (3'-C), 111.12 (4'-C), 107.68 (3-C), 105.29 (2-C), 61.90 (—CMe3), 36.04 (1"-C), 31.58 (3-C), 30.71 (2"-C), 30.04 (—C(CH3)3), 22.65 (4"-C), 14.16 (5"-C). HPLC-MS: [A, 50-95%], $t_R$=2.36 min, (99%); MS (ES+) m/z=303 $[M+H]^+$. Anal. calcd. for C18H26N2O2: C: 71.49%; H: 8.67%, N: 9.26%, found: C: 70.15%; H: 8.56%; N: 8.62%. 2-[1-(Tert-butyl)-1H-pyrazol-3-yl]-5-pentylbenzene-1,3-diol: 1H-NMR (400 MHz, CDCl3) δ: 8.40 (bs, 2H, —OH), 7.56 (d, J=2.5 Hz, 1H, 5'-H), 6.94 (d, J=2.5 Hz, 1H, 4'-H), 6.33 (s, 2H, 3-H), 2.54-2.38 (m, 2H, 1"-H), 1.69-1.50 (m, 11H, 2"-H, —C(CH3)3), 1.34-1.28 (m, 4H, 3"-H, 4"-H), 0.91-0.84 (m, 3H, 5"-H). 13C-NMR (101 MHz, CDCl3) δ: 155.72 (1-C), 147.63 (2-C), 144.31 (5-C), 126.21 (5'-C), 108.31 (3-C), 105.79 (4'-C), 103.55 (2-C), 58.71 (—CMe3), 35.80 (1"-C), 31.58, 22.71 (3"-C, 4"-C), 30.76 (2"-C), 29.79 (—C(CH3)3), 14.18 (5"-C). HPLC-MS: [A, 50-95%], $t_R$=7.25 min, (99%); MS (ES+) m/z=303 $[M+H]^+$.

Example 13. 2-(1-Cyclohexyl-1H-pyrazol-5-yl)-5-pentylbenzene-1,3-diol

A solution of 5-hydroxy-7-pentyl-4H-chromen-4-one (100.0 mg; 0.43 mmol) in 5 mL of ethanol was incorporated to a 10 mL suspension of cyclohexylhydrazine hydrochloride (258.6 mg; 1.72 mmol) and sodium hydroxide (69.0 mg; 1.72 mmol). The mixture was refluxed overnight and then, the mixture was dissolved in $H_2O$. The organic layer was extracted with EtOAc/Brine, dried over $MgSO_4$ and the solvent was removed under vacuum. The resultant yellow oil was purified by medium pressure column chromatography in 15-70% of ethyl acetate in hexane to obtain 104.1 mg of a light yellow oil (yield=74%): 1H-NMR (400 MHz, CDCl3) δ: 7.67 (d, J=1.8 Hz, 1H, 5'-H), 6.43 (s, 2H, 3-H), 6.41-6.32 (bs, 2H, —OH), 6.30 (d, J=1.8 Hz, 1H, 4'-H), 3.89 (p, J=8.4

Hz, 1H, 1Cy-H), 2.53 (t, J=7.6 Hz, 2H, 1"-H), 1.96-1.84 (m, 4H, 2Cy-H), 1.80-1.71 (m, 2H, 2"-H), 1.67-1.55 (m, 4H, 3Cy-H), 1.37-1.30 (m, 4H, 3"-H, 4"-H), 1.23-1.10 (m, 2H, 4Cy-H), 0.89 (t, J=4.2 Hz, 3H, 5"-H). 13C-NMR (101 MHz, CDCl3) δ: 155.0 (1-C), 147.18 (5-C), 139.46 (5'-C), 132.69 (3'-C), 107.69 (3-C), 107.06 (4'-C), 102.13 (2-C), 58.68 (1Cy-C), 36.09 (1"-C), 33.06 (3Cy-C), 21.63 (4"-C), 30.68 (2Cy-C), 25.74 (2"-C), 25.22 (4Cy-C), 22.64 (3"-C), 14.12 (5"-C). HPLC-MS: [A, 80-95%], $t_R$=3.53 min, (99%); MS (ES+) m/z=329 [M+H]$^+$. Anal. calcd. for C20H28N2O2: C: 73.14%; H: 8.59%, N: 8.53%, found: C: 72.49%; H: 8.66%; N: 8.21%.

Example 14. 5-Pentyl-2-(1-phenyl-1H-pyrazol-5-yl)benzene-1,3-diol

To a solution of 5-hydroxy-7-pentyl-4H-chromen-4-one (200.0 mg, 0.86 mmol) in 15 mL of EtOH, phenylhydrazine (340 μL, 3.45 mmol) was added and the reaction was refluxed overnight. Then, the reaction was cooled down, and diluted with H2O. The organic layer was extracted with CH$_2$Cl$_2$, dried over MgSO$_4$ and the solvent removed under vacuum. Afterwards, the resultant dark oil was purified by medium pressure column chromatography (ethyl acetate/hexane, 3:1) giving a brown solid (119.8 mg, yield=43%): 1H-NMR (400 MHz, CDCl3) δ: 7.76 (d, J=1.8 Hz, 1H, 5'-H), 7.37-7.03 (m, 5H, 2a-H, 3a-H, 4a-H), 6.48 (d, J=1.8 Hz, 1H, 4'-H), 6.21 (s, 2H, 3-H), 2.40 (t, J=7.5 Hz, 2H, 1"-H), 1.49 (p, J=7.5 Hz, 2H, 2"-H), 1.29-1.19 (m, 4H, 3"-H, 4"-H), 0.82 (t, J=6.9 Hz, 3H. 5"-H). 13C-NMR (101 MHz, CDCl3) δ: 154.29 (1-C), 147.49 (5-C), 141.12 (5'-C), 139.96 (1a-C), 133.04 (3'-C), [128.95, 127.57 (3a-C, 4a-C)], 123.50 (2a-C), 110.04 (4'-C), 108.01 (3-C), 102.67 (2-C), 35.99 (1"-C), 31.53 (3"-C), 30.58 (2"-C), 22.65 (4"-C), 14.17 (5"-C). HPLC-MS: [A, 15-95%], $t_R$=6.25 min, (99%); MS (ES+) m/z=323 [M+H]$^+$. Anal. calcd. for C14H16O3: C: 74.51%; H: 6.88%, N: 8.69%, found: C: 73.91%; H: 7.07%; N: 8.24%.

Example 15. 2-(1-Benzyl-1H-pyrazol-5-yl)-5-pentylbenzene-1,3-diol and 2-(1-benzyl-1H-pyrazol-3-yl)-5-pentylbenzene-1,3-diol A suspension of benzylhydrazine dihydrochloride (672.4 mg, 3.45 mmol) in 10 mL of ethanol was neutralized with sodium hydroxide pellets (275.9 mg, 6.90 mmol). Then, a solution of 5-hydroxy-7-pentyl-4H-chromen-4-one in 4 mL of ethanol was added (168.0 mg, 0.72 mmol) and the mixture was refluxed for 3 h. After completion, the reaction was cooled down and diluted with H$_2$O. Then, the organic layer was extracted with ethyl acetate, dried over MgSO$_4$ and the solvent was removed under vacuum. The crude mixture was the purified by medium pressure column chromatography in 17 to 25% ethyl acetate in hexane giving a pale-yellow oil (214.9 mg, yield=85%; 2-(1-Benzyl-1H-pyrazol-5-yl)-5-pentylbenzene-1,3-diol) and another pale-yellow oil (34.7 mg, yield=14%; 2-(1-benzyl-1H-pyrazol-3-yl)-5-pentylbenzene-1,3-diol).

2-(1-Benzyl-1H-pyrazol-5-yl)-5-pentylbenzene-1,3-diol: 1H-NMR (400 MHz, CDCl3) δ: 7.65 (d, J=2.0 Hz, 1H, 5'-H), 7.19-7.13 (m, 3H, 3a-H, 4a-H), 7.01-6.95 (m, 2H, 2a-H), 6.37 (d, J=2.0 Hz, 1H, 4'-H), 6.36 (s, 2H, 3-H), 6.23 (—OH, bs, 2H), 5.16 (s, 2H, 2"-NCH2), 2.50 (t, J=7.7 Hz, 2H, 1"-H), 1.60 (p, J=7.6 Hz, 2H, 2"-H), 1.41-1.29 (m, 4H, 3"-H, 4"-H), 0.92 (t, J=6.6 Hz, 3H, 5"-H). 13C-NMR (101 MHz, CDCl3) δ: 154.81 (1-C), 147.51 (3'-C), 139.90 (5'-C), 136.59 (1a-C), 133.98 (3'-C), [128.60, 127.91 (2a-C), (3a-C)], 127.84 (4a-C), 108.22 (4'-C), 107.85 (3-C), 101.99 (2-C), 53.92 (2"-NCH2), 36.04 (1"-C), 31.56 (3"-C), 30.73 (2"-C), 22.67 (4"-C), 14.17 (5"-C). HPLC-MS: [A, 50-95%], $t_R$=2.22 min, (96%); MS (ES+) m/z=337 [M+H]$^+$. Anal. calcd. for C21H24N2O2: C: 74.97%; H: 7.19%, N: 8.33%, found: C: 74.57%; H: 7.18%; N: 8.32%. 2-(1-Benzyl-1H-pyrazol-3-yl)-5-pentylbenzene-1,3-diol: 1H-NMR (400 MHz, CDCl3) δ: 8.68 (—OH, bs, 2H), 7.30 (d, J=2.4 Hz, 1H, 5'-H), 7.28-7.16 (m, 3H, 3a-H, 4a-H), 7.16-7.06 (m, 2H, 2a-H), 6.95 (d, J=2.4 Hz, 1H, 4'-H), 6.24 (s, 2H, 3-H), 5.21 (s, 2H, 1"-NCH2), 2.36 (t, J=7.7 Hz, 2H, 1"-H), 1.51-1.43 (m, 2H, 2"-H), 1.23-1.13 (m, 4H, 3-H, 4"-H), 0.78 (t, J=6.4 Hz, 3H, 5"-H). 13C-NMR (101 MHz, CDCl3) δ: 155.78 (1-C), 148.76 (3'-C), 144.48 (5'-C), 136.07 (1a-C), 129.77 (3'-C), [128.96, 128.30 (2a-C, 3a-C)], 127.80 (4a-C), 108.31 (4'-C), 107.19 (3-C), 103.31 (2-C), 56.00 (1"-NCH2), 35.76 (1"-C), 31.56 (3"-C), 30.68 (2"-C), 22.65 (4"-C), 14.15 (5"-C). HPLC-MS: [A, 50-95%], $t_R$=6.86 min, (91%); MS (ES+) m/z=337 [M+H]$^+$. Anal. calcd. for C21H24N2O2: C: 74.97%; H: 7.19%, N: 8.33%, found: C: 75.03%; H: 7.23%; N: 8.22%.

Example 16. 5-(1',1'-Dimethylhept-1-yl)-2-(1H-pyrazol-3-yl)benzene-1,3-diol

To a stirring solution of 5-hydroxy-7-(1',1'-dimethylheptyl-1-yl)-4H-chromen-4-one (72.0 mg, 0.25 mmol) in 6 mL of EtOH, hydrazine hydrate (48 μL, 1.00 mmol) was incorporated and the reaction was refluxed for 45 min. Then, the solvent was removed under vacuum and the resultant yellow oil was purified by medium pressure column chromatography (ethyl acetate/hexane 1:2) giving a white solid (38.4 mg, yield=51%): 1H-NMR (400 MHz, MD3OD) δ: 7.66 (d, J=2.5 Hz, 1H, 5'-H), 7.12 (d, J=2.3 Hz, 1H, 4'-H), 6.46 (s, 2H, 3-H), 1.62-1.56 (m, 2H, 2"-H), 1.26 (s, 6H, 8"-H), 1.25-1.19 (m, 6H, 3-H, 4"-H, 5"-H), 1.18-1.07 (m, 2H, 6"-H), 0.87 (t, J=6.7 Hz, 3H, 7"-H). 13C-NMR (101 MHz, MD3OD) δ: 157.37 (1-C), 153.26 (5-C), 151.85 (3'-C), 129.38 (5'-C), 106.95 (4'-C), 106.06 (3-C), 103.97 (2-C), 45.49 (1"-C), 38.38 (2"-C), 32.91 (5"-C), 31.14 (4"-C), 29.37 (8"-C), 25.81 (3"-C), 23.66 (6"-C), 14.39 (7"-C). HPLC-MS: [A, 80-95%], $t_R$=1.04 min, (96%); MS (ES+) m/z=303 [M+H]$^+$. Anal. calcd. for C18H26N2O2: C: 71.49%; H: 8.67%, N: 9.26%, found: C: 71.48%; H: 8.97%; N: 8.60%.

Example 17. 2-(1-Isopropyl-1H-pyrazol-5-yl)-5-(1',1'-dimethylhepthyl-1-yl)benzene-1,3-diol and 2-(1-isopropyl-1H-pyrazol-3-yl)-5-(1',1'-dimethylhepthyl-1-yl)benzene-1,3-diol Isopropylhydrazine hydrochloride (362.3 mg, 3.26 mmol) was added to a solution of 5-hydroxy-7-(1',1'-dimethylhepthyl-1-yl)-4H-chromen-4-one (235.0 mg, 0.82 mmol) in 10 mL of EtOH and the mixture was neutralized with a few drops of NaOH 1 N and then refluxed for 2 days. After completion, the reaction was cooled down and diluted with H$_2$O. Then, the organic layer was extracted with CH$_2$Cl$_2$, dried over MgSO$_4$ and the solvent was removed under vacuum. The crude mixture was purified by medium pressure column chromatography a gradient of 15-30% of ethyl acetate in hexane giving a yellow oil (98.3.0 mg, yield=42%; 2-(1-Isopropyl-1H-pyrazol-5-yl)-5-(1',1'-dimethylhepthyl-1-yl)benzene-1,3-diol) and a mixture that was then purified by SPE cartridge using 1:1 dichloromethane/hexane as eluent giving a white solid (12.0 mg; yield=5%; 2-(1-isopropyl-1H-pyrazol-3-yl)-5-(1',1'-dimethylhepthyl-1-yl)-benzene-1,3-diol).

2-(1-Isopropyl-1H-pyrazol-5-yl)-5-(1',1'-dimethylheptyl-1-yl)benzene-1,3-diol: 1H-NMR (400 MHz, CDCl3) δ: 7.70 (d, J=1.8 Hz, 1H, 5'-H), 6.57 (s, 2H, 3-H), 6.32 (d, J=1.8 Hz, 1H, 4'-H), 4.36 (hept, J=6.8 Hz, 1H, CH), 1.59-1.52 (m, 2H, 2"-H), 1.42 (d, J=6.7 Hz, 6H, CH(CH3)2), 1.24 (s, 6H; 8"-H), 1.24-1.18 (m, 6H, 3-H, 4"-H, 5"-H), 1.16-1.07 (m, 2H, 6"-H), 0.85 (t, J=6.7 Hz, 3H, 7"-H). 13C-NMR (101 MHz, CDCl3) δ: 154.83 (1-C), 154.48 (5-C), 139.56 (5'-C), 132.79 (3'-C), 107.00 (4'-C), 105.48 (3-C), 101.77 (2-C), 50.96 (CH), 44.53 (2"-C), 38.01 (1"-C), 31.89 (5"-C), 30.09 (4"-C), 28.83 (8"-C), 24.76 (6"-C), 22.76 (CH(CH3)2), 21.15 (3-C), 14.18 (7"-C). HPLC-MS: [A, 50-95%], $t_R$=4.55 min, (96%); MS (ES+) m/z=345 [M+H]$^+$. Anal. calcd. for C21H32N2O2: C: 73.22%; H: 9.36%, N: 8.13%, found: C: 72.36%; H: 9.32%; N: 7.69%.

2-(1-Isopropyl-1H-pyrazol-3-yl)-5-(1',1'-dimethylheptyl-1-yl)benzene-1,3-diol: 1H-NMR (400 MHz, CDCl3) δ: 8.31 (s, 2H, OH), 7.47 (d, J=2.5 Hz, 1H, 5'-H), 6.95 (d, J=2.4 Hz, 1H, 4'-H), 6.47 (s, 2H, 3-H), 4.53 (hept, J=6.7 Hz, 1H, CH), 1.60-1.50 (m, 8H, CH(CH3)2, 2"-H), 1.24 (s, 6H, 8"-H), 1.23-1.14 (m, 6H, 3-H, 4"-H, 5"-H), 1.13-1.02 (m, 2H, 6"-H), 0.84 (t, J=6.8 Hz, 3H, 7"-H). 13C-NMR (101 MHz, CDCl3) δ: 155.38 (1-C), 151.47 (5-C), 147.72 (3'-C), 127.14 (5'-C), 106.21 (3-C), 105.94 (4'-C), 103.24 (2-C), 53.85 (CH), 44.60 (2"-C), 37.75 (1"-C), 31.97 (5"-C), 30.21 (4"-C), 28.94 (8"-C), 24.85 (6"-C), 22.87 (CH(CH3)2), 22.83 (3-C), 14.23 (7"-C). HPLC-MS: [A, 50-95%], $t_R$=7.23 min, (99%); MS (ES+) m/z=345 [M+H]$^+$.

Example 18. 2-(1-Benzyl-1H-pyrazol-3-yl)-4-fluoro-5-pentylbenzene-1,3-diol

1-Fluoropyridinium triflate (36.1 mg, 0.15 mmol) was added to a solution of 2-(1-benzyl-1H-pyrazol-3-yl)-5-pentylbenzene-1,3-diol (49.0 mg, 0.15 mmol) in 2 mL of anhydrous CH$_2$Cl$_2$ and the reaction was stirred at rt for 6 h. After that time, the reaction was diluted with CH$_2$Cl$_2$ and washed with a saturated aqueous solution of NaHCO$_3$. The organic layer was separated, dried over MgSO$_4$, and evaporated. Then, the mixture was purified by chromatographic techniques. First, the crude mixture was purified by column chromatography in 2:1 dichloromethane:hexane to remove the remaining starting product. Afterwards, the recovered white solid was purified again by semipreparative HPLC to give a white solid (9.4 mg, yield=18%): 1H-NMR (400 MHz, CDCl3) δ: 10.34 (s, 1H, 8-H), 7.36 (d, J=2.4 Hz, 1H, 5'-H), 7.30-7.22 (m, 3H, H, 3a-H and 4a-H), 7.19-7.13 (m, 2H, 2a-H), 7.00 (d, J=2.4 Hz, 1H, 4'-H), 6.32 (bs, 1H, 7-H), 6.27 (d, JH-F=6.3 Hz, 1H, 6-H), 5.26 (s, 2H, CH2), 2.51 (t, J=7.6 Hz, 2H, 1"-H), 1.53 (p, J=7.3 Hz, 2H, 2"-H), 1.34-1.17 (m, 4H, 3-H and 4"-H), 0.87-0.72 (m, 3H, 5"-H). 13C-NMR (101 MHz, CDCl3) δ: 152.00 (d, JC-F=2.2 Hz, 1-C), 148.25 (d, JC-F=3.4 Hz, 3'-C), 143.87 (d, JC-F=224.0 Hz, 4-C), 142.11 (d, JC-F=17.5 Hz, 3-C), 135.96 (1a-C), 129.84 (5'-C), 129.42 (d, JC-F=15.6 Hz, 5-C), 129.04 (3a-C), 128.43 (4a-C), 127.87 (2a-C), 108.05 (d, JC-F=4.0 Hz, 6-C), 107.28 (4'-C), 104.29 (2-C), 56.14 (CH2), 31.55 (3"-C), 29.69 (2"-C), 28.98 (d, JC-F=1.6 Hz, 1"-C), 22.62 (4"-C), 14.15 (5"-C). HPLC-MS: [A, 50-95%], $t_R$=7.27 min, (99%); MS (ES+) m/z=355 [M+H]$^+$. Anal. calcd. for C21H23FN2O2: C: 71.17%; H: 6.54%; F: 5.36%; N: 7.90%; found: C: 69.94%; H: 6.90%; N: 6.97%.

Example 19. 2-[1-(3-Hydroxybenzyl)-1H-pyrazol-5-yl]-5-pentylbenzene-1,3-diol Boron tribromide 1M solution in CH$_2$Cl$_2$ (244 μL, 0.24 mmol) was carefully added to a stirring solution of 2-[1-(3-methoxybenzyl)-1H-pyrazol-5-yl]-5-pentylbenzene-1,3-diol (35.8 mg, 0.10 mmol) in 3 mL of anhydrous CH$_2$Cl$_2$ under N$_2$ atmosphere at −78° C. The mixture was stirred under those conditions O/N. Then, additional boron tribromide solution was added (500 μL, 0.5 mmol) and the mixture was stirred O/N. After that time, methanol was added to the mixture to neutralize the remaining boron tribromide and the solvent was removed under vacuum. The crude mixture was dissolved in EtOAc/H$_2$O and the organic layer was extracted with EtOAc. The combined organic layers were dried over MgSO$_4$, filtered, and the solvent was removed under vacuum. The resultant oil was purified by column chromatography in hexane/ethyl acetate to provide oil (27.6 mg, yield=84%): 1H-NMR (300 MHz, CDCl3) δ: 7.53 (d, J=1.9 Hz, 1H, 5'-H), [6.87 (t, J=8.0 Hz, 1H), 6.54-6.48 (m, 1H), 6.41-6.35 (m, 2H); ar-H], 6.32 (s, 2H, 3-H), 6.30 (d, J=1.9 Hz, 1H, 4'-H), 4.97 (s, 2H, —NCH2-), 2.44 (t, J=7.7 Hz, 2H, 1"-H), 1.54 (p, J=7.2 Hz, 2H, 2"-H), 1.36-1.26 (m, 4H, 3-H, 4"-H), 0.92-0.82 (m, 3H, 5"-H). 13C-NMR (75 MHz, CDCl3) δ: 156.13 (2a-C), 154.79 (1-C), 147.63 (5-C), 139.69 (5'-C), 137.90 (1a-C), 135.04 (3'-C), 129.77, 119.52, 115.26, 114.84 (ar-C), 108.33 (4'-C), 108.11 (3-C), 101.88 (2-C), 53.23 (—NCH2-), 36.01 (1"-C), 31.60 (3"-C), 30.68 (2"-C), 22.65 (4"-C), 14.17 (5"-C). HPLC-MS: [A, 30-95%], $t_R$=5.88 min, (99%); MS (ES+) m/z=353 [M+H]$^+$.

Example 20. 2-[1-(4-Hydroxybenzyl)-1H-pyrazol-5-yl]-5-pentylbenzene-1,3-diol Boron tribromide 1M solution in CH$_2$Cl$_2$ (702 μL, 0.70 mmol) was carefully added to a stirring solution of 2-[1-(4-methoxybenzyl)-1H-pyrazol-5-yl]-5-pentylbenzene-1,3-diol (102.8 mg, 0.28 mmol) in 5 mL of anhydrous CH$_2$Cl$_2$ under N2 atmosphere at −78° C. The mixture was stirred under those conditions O/N. After that time, methanol was added to the mixture to neutralize the remaining boron tribromide and the solvent was removed under vacuum. The crude mixture was dissolved in EtOAc/H$_2$O and the organic layer was extracted with EtOAc (×3). The combined organic layers were dried over MgSO$_4$, filtered, and the solvent was removed under vacuum. The resultant oil was purified by medium pressure column chromatography in 30%-80% ethyl acetate in hexane to provide a white solid (37.3 mg, yield=37%): 1H-NMR (300 MHz, CD3OD) δ: 7.50 (d, J=1.9 Hz, 1H, 5'-H), 6.93-6.85 (m, 2H, 2a-H), 6.65-6.55 (m, 2H, 3a-H), 6.27 (s, 2H, 3-H), 6.23 (d, J=1.9 Hz, 1H, 4'-H), 5.04 (s, 2H, —NCH2-), 2.49 (t, J=7.6 Hz, 2H, 1"-H), 1.62 (p, J=7.2 Hz, 2H, 2"-H), 1.47-1.23 (m, 4H, 3-H, 4"-H), 1.04-0.80 (m, 3H, 5"-H). 13C-NMR (75 MHz, CD3OD) δ: 157.69 (4a-C), 157.57 (1-C), 147.41 (5-C), 139.26 (5'-C), 138.29 (3'-C), 130.17 (2a-C), 129.57 (1a-C), 115.88 (3a-C), 108.75 (4'-C), 107.86 (3-C), 103.94 (2-C), 53.87 (—NCH2-), 36.89 (1"-C), 32.55 (3-C), 31.93 (2"-C), 23.58 (4"-C), 14.41 (5"-C). HPLC-MS: [A, 30-95%], $t_R$=5.78 min, (97%); MS (ES+) m/z=353 [M+H]$^+$.

Example 21. 2-[1-(3-Hydroxybenzyl)-1H-pyrazol-3-yl]-5-pentylbenzene-1,3-diol Boron tribromide 1M solution in CH2Cl2 (385 μL, 0.38 mmol) was carefully added to a stirring solution of 2-[1-(3-methoxybenzyl)-1H-pyrazol-3-yl]-5-pentylbenzene-1,3-diol (70.5 mg, 0.19 mmol) in 2 mL of anhydrous CH$_2$Cl$_2$ under N$_2$ atmosphere at −78° C. The mixture was stirred under those conditions. Afterwards, additional boron tribromide solution was added (288 μL, 0.29 mmol) and the mixture was stirred. Methanol was added to the mixture to neutralize the remaining boron tribromide and the solvent was removed under vacuum. The crude mixture was redissolved in EtOAc/H$_2$O and the organic layer was extracted with EtOAc. The combined organic layers were dried over MgSO$_4$, filtered, and the solvent was removed under vacuum. The resultant oil was purified by column chromatography in 4:1 hexane/ethyl acetate to provide an oil (49.7 mg, yield=67%): 1H-NMR (300 MHz, CDCl3) δ: 8.51 (s, 2H, —OH), 7.41 (d, J=2.4 Hz, 1H, 5'-H), 7.18 (t, J=7.9 Hz, 1H, ar-H), 7.00 (d, J=2.4 Hz, 1H, 4'-H), 6.83-6.73 (m, 2H, ar-H), 6.69-6.61 (m, 1H, ar-H), 6.34 (s, 2H, 3-H), 5.61 (s, 1H, —OH), 5.24 (s, 2H, —NCH2-), 2.53-2.42 (m, 2H, 1"-H), 1.58 (p, J=7.5 Hz, 2H, 2"-H), 1.36-1.28 (m, 4H, 3-H, 4"-H), 0.94-0.82 (m, 3H, 5"-H). 13C-NMR (75 MHz, CDCl3) δ: 156.29 (2a-C), 155.65 (1-C), 148.65 (3'-C), 144.61 (5-C), 137.81 (1a-C), 130.26 (ar-C), 129.98 (5'-C), 119.92, 115.45, 114.62 (ar-C), 108.44 (3-C), 107.18 (4'-C), 103.33 (2-C), 55.76 (—NCH2-), 35.78 (1"-C), 31.58 (3-C), 30.71 (2"-C), 22.68 (4"-C), 14.16 (5"-C). HPLC-MS: [A, 50-95%], $t_R$=4.50 min, (91%); MS (ES+) m/z=353 [M+H]$^+$.

Example 22. 2-[1-(4-Hydroxybenzyl)-1H-pyrazol-3-yl]-5-pentylbenzene-1,3-diol

Boron tribromide 1M solution in CH$_2$Cl2 (340 μL, 0.34 mmol) was carefully added to a stirring solution of 2-[1-(4-methoxybenzyl)-1H-pyrazol-3-yl]-5-pentylbenzene-1,3-diol (50.1 mg, 0.14 mmol) in 2.5 mL of anhydrous CH$_2$Cl$_2$ under N$_2$ atmosphere at −78° C. The mixture was stirred under those conditions O/N. After that time, 2.5 mL of methanol were added to the mixture to neutralize the remaining boron tribromide and the solvent was removed under vacuum. The crude mixture was redissolved in EtOAc/H$_2$O and the organic layer was extracted with EtOAc. The combined organic layers were dried over MgSO$_4$, filtered, and the solvent was removed under vacuum. The resultant oil was purified by medium pressure column chromatography in 4:1 hexane/ethyl acetate to provide a pale-yellow solid (17.0 mg, yield=37%). 1H-NMR (300 MHz, CD3OD) δ: 7.56 (d, J=2.4 Hz, 1H, 5'-H), 7.20-7.09 (m, 2H, 2a-H), 7.04 (d, J=2.4 Hz, 1H, 4'-H), 6.81-6.70 (m, 2H, 3a-H), 6.25 (s, 2H, 3-H), 5.23 (s, 2H, —NCH2-), 2.45 (t, J=7.6 Hz, 2H, 1"-H), 1.59 (p, J=7.4 Hz, 2H, 2"-H), 1.41-1.26 (m, 4H, 3-H, 4"-H), 0.90 (t, J=6.8 Hz, 3H, 5"-H). 13C-NMR (75 MHz, CD3OD) δ: 158.47 (4a-C), 157.74 (1-C), 150.38 (3'-C), 144.90 (5-C), 130.52 (5'-C), 130.48 (2a-C), 128.74 (1a-C), 116.44 (3a-C), 108.21 (3-C), 107.99 (4'-C), 104.35 (2-C), 56.14 (—NCH2-), 36.74 (1"-C), 32.62 (3-C), 31.90 (2"-C), 23.59 (4"-C), 14.38 (5"-C). HPLC-MS: [A, 50-95%], $t_R$=4.38 min, (96%); MS (ES+) m/z=353 [M+H]$^+$.

Example 23. Biological Assays

In the present invention, the activity of the compounds of the invention on the GPR18 receptor was assessed by performing in vitro assays in transfected cells expressing GPR18 or TRPV1.

Methods
Cell Culture.

A plasmid containing GPR18 (NM_005292) was obtained from Origene (Rockville, MD) and engineered with an N-terminal GFP-tag. The resulting plasmid was used to transfect CHO-K1 cells using Lipofectamine 2000 (Invitrogen, Carlsbad CA). Clonal cells were selected in medium containing G418 (Geneticin, 800 μg/ml; Enzo Life Sciences, Farmingdale, NY). Two weeks after transfection, clones were isolated and expression was verified by fluorescence microscopy of GFP-tagged receptors. The resulting stable cell line was cultured in DMEM with 10% fetal bovine serum at 37° C., 5% CO$_2$ and passaged every 2-3 days. PathHunter® β-arrestin CHO-K1/GPR18 cells (Eurofins/DiscoveRx, Fremont, CA, USA) were maintained in PathHunter® select cell culture media at 37° C., 5% CO$_2$ (according to the manufacturer specifications, and passaged every 2-3 days for a maximum of 10 passages as previously published (Console-Bram, 2014). A plasmid containing Human TRPV1 (NM_018727) with a C-terminal flag tag was obtained from Genscript (Piscataway, NJ, USA) and used to transfect HEK293 cells using Lipofectamine 2000 (Invitrogen, Carlsbad CA). Clonal cells were selected in medium containing G418 (Geneticin, 800 μg/ml; Enzo Life Sciences, Farmingdale, NY). Two weeks after transfection, clones were isolated and expression was verified by fluorescence microscopy of HA-tagged receptors. The resulting stable cell line was cultured in DMEM with 10% fetal bovine serum at 37° C., 5% CO$_2$ and passaged every 2-3 days.

Calcium Imaging.

Intracellular Ca$^{2+}$ measurements were performed as described (Console-Bram, 2014). Briefly, Cells were grown in 25 mm coverslips coated with Poly-D-Lysine until 30-50% confluent, and incubated with 4 μM Fura-2 AM (Invitrogen) in HBSS with calcium and magnesium for 45 min at room temperature and in the dark. Then, cells were washed in dye-free HBSS and coverslips were mounted in an open bath chamber (QR-40LP, Warner Instruments, Hamden, CT) on the stage of a Nikon Eclipse TiE inverted microscope (Nikon Inc., Melville, NY, USA) equipped with a Perfect Focus System and a Photometrics CoolSnap HQ2 charge-coupled device camera (Photometrics, Tucson, AZ, USA). Intracellular calcium levels were determined by measuring fluorescence emissions from Fura-2 AM (510 nm) after alternating excitation at 340 and 380 nm at 0.25 Hz for 5 min. Images were analyzed in the NIS-Elements AR software (Nikon), and the fluorescence ratio at 340 nm/380 nm was converted to Ca$^{2+}$ concentrations.

β-Arrestin Translocation Assay.

Quantification of β-arrestin recruitment was accomplished using DiscoveRx PathHunter® CHO-K1 cells stably expressing GPR18 fused with a β-galactosidase enzyme fragment, and β-arrestin fused to an N-terminal deletion mutant of β-galactosidase. Activation of GPR18 induces β-arrestin recruitment, forcing complementation of the two β-galactosidase enzyme fragments. Levels of this active enzyme are a direct result of GPR18 activation and are quantitated using chemiluminescent PathHunter® detection reagents containing the β-galactoside substrate. Cells were plated in 384-well plates at 5,000 cells/well in the manufacturer's cell plating 1 reagent overnight. Cells were then incubated with compounds for 90 min at 37° C. Compounds were dissolved in DMSO and serial dilutions were made in cell plating 1 reagent. Following a 1-hour incubation (RT) in detection reagent, the chemiluminesence signal was measured using a Perkin Elmer Envision plate reader for 1 second. Relative luminescence units were normalized to vehicle treated samples. Data was fit to a three-parameter nonlinear regression analysis using GraphPad Prism (GraphPad Software, LaJolla, CA).

Results
GPR18 Activity

FIG. 1 demonstrates that S9 (10 μM) increases intracellular calcium (Ca$^{2+}$) in a GPR18 expressing cell line. Panel A shows representative examples of F340/F380 ratio before (basal) and after treatment with 10 μM S9. B. Representative examples of S9-induced increase in $[Ca^{2+}]_i$. C. Quantification of response. n=45-50 cells.

Figure 2:
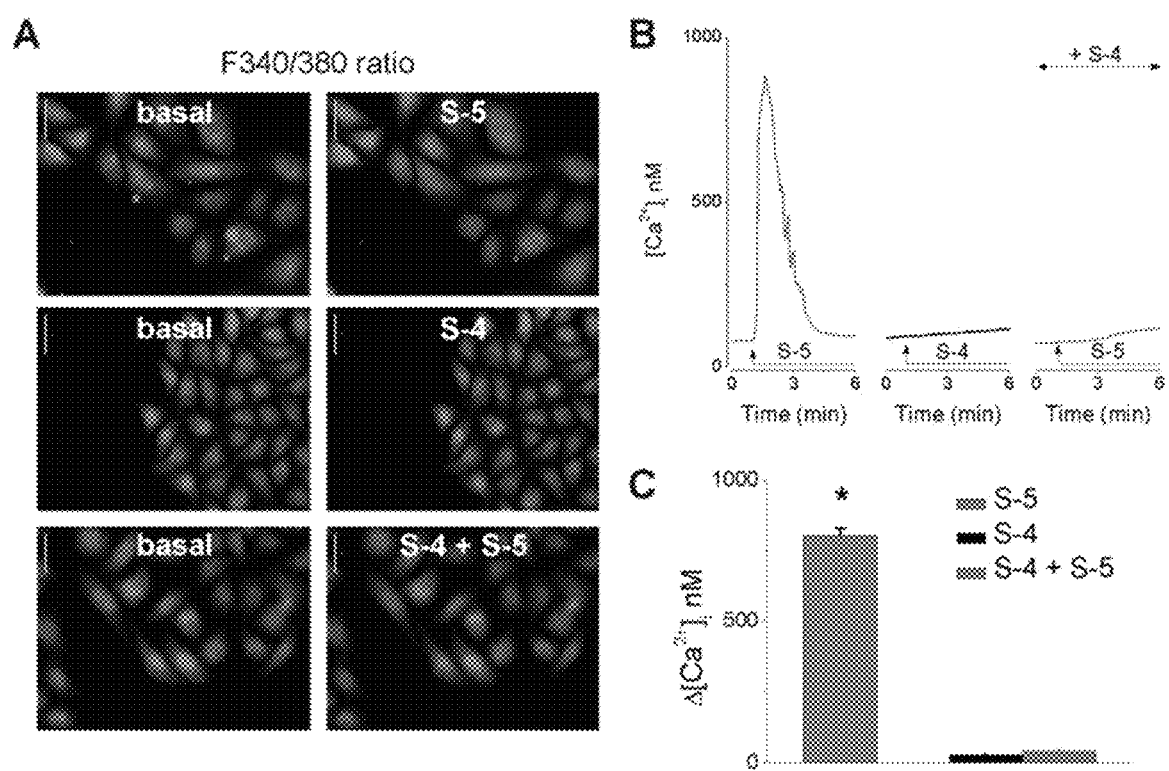
FIG. 2. Effect of S5 (10 □µM) on intracellular calcium ($Ca^{2+}$) in a GPR18 expressing cell line. A. F340/F380 ratio before (basal) and after treatment with 10 µM S5, 10 µM S4 or 10 µM S4+10 µM S5. B. S5-induced increase in $[Ca^{2+}]_i$, which is blocked by S4. S4 was applied 10 minutes before S5. C. Quantification of response. n=45-50 cell.

FIG. 2 demonstrates that S5 (10 μM) increases intracellular calcium ($Ca^{2+}$) in a GPR18 expressing cell line. This increase in $[Ca^{2+}]_i$ is blocked with equimolar concentrations of S4, which on its own has no effect on $[Ca^{2+}]_i$. Panel A shows representative examples of F340/F380 ratio before (basal) and after treatment with 10 μM S5, 10 μM S4 or 10 μM S4+10 μM S5. B. Representative examples of S5-induced increase in $[Ca^{2+}]_i$, which is blocked by S4. S4 was applied 10 minutes before S5. C. Quantification of response. n=45-50 cell.

Figure 3:
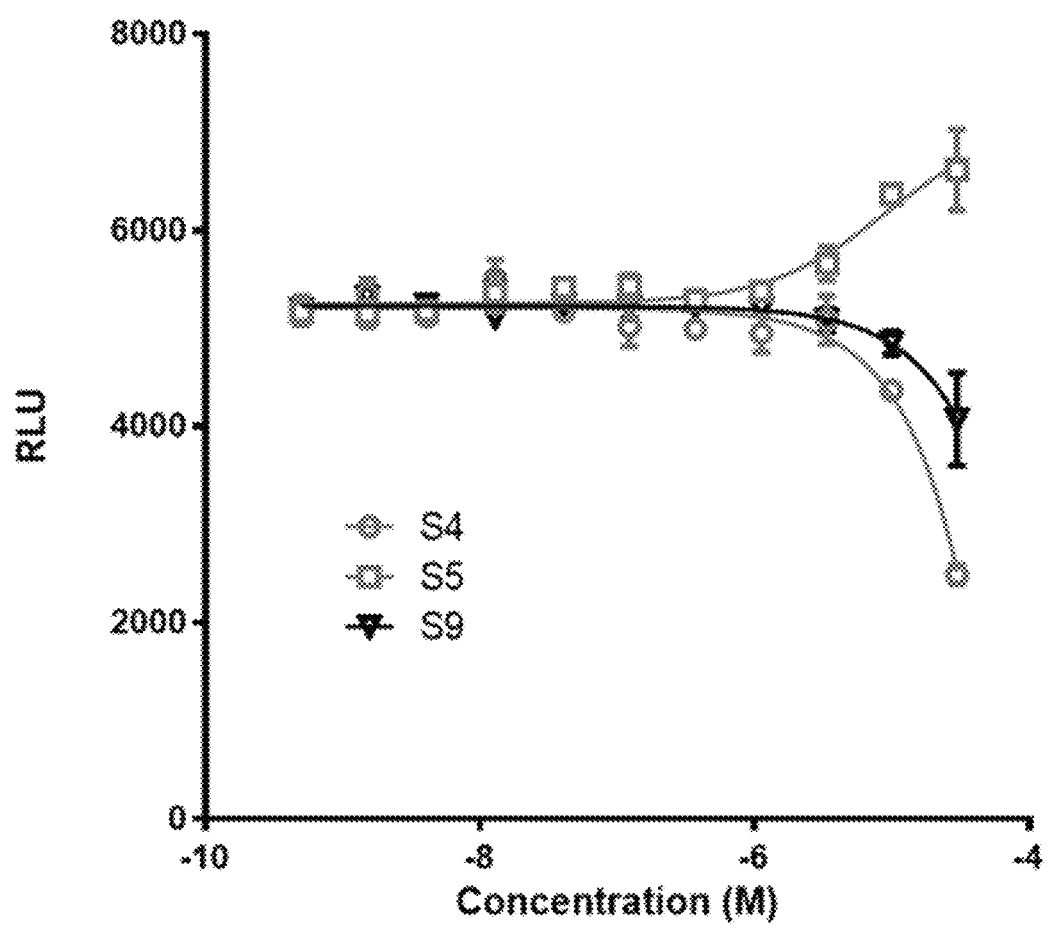
FIG. 3. Effect of S5 in the β-arrestin2 complementation assay at 10 and 30 µM. Data shown are the results of three experiments performed in triplicate.

FIG. 3 demonstrates that S5 is an agonist in the β-arrestin2 complementation assay, whereas S4 shows inverse agonist activity at 10 and 30 μM. S9 shows inverse agonist activity at 30 μM. S5 has an EC50 of 9 μM in this assay. Data shown are the results of three experiments performed in triplicate.

TPRV1 Activity

Figure 4:
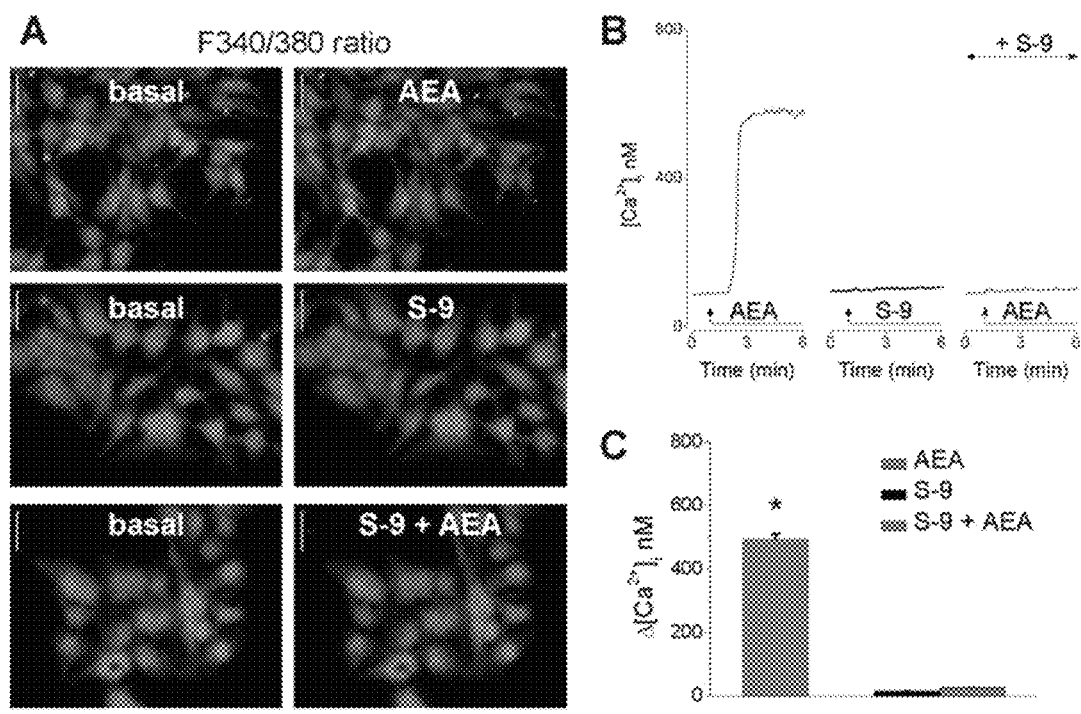
FIG. 4. Effect of S9 in TPRV1-expressing cells. A. F340/F380 ratio before (basal) and after treatment with 10 µM S5, 10 µM S4 or 10 µM S4+10 µM S5. B. S5-induced increase in $[Ca^{2+}]_i$, blocked by S4. S9 was applied 10 minutes before AEA. C. Quantification of response. n=45-50 cell.

FIG. 4 demonstrates that S9 acts as an antagonist in TPRV1-expressing cells. Anandamide (AEA, 5 μM) increases intracellular calcium ($Ca^{2+}$). This increase in $[Ca^{2+}]_i$ is blocked by S9 (10 μM), which on its own has no effect on $[Ca^{2+}]_i$. Panel A shows representative examples of F340/F380 ratio before (basal) and after treatment with 10 μM S5, 10 μM S4 or 10 μM S4+10 μM S5. B. Representative examples of S5-induced increase in $[Ca^{2+}]_i$, which is blocked by S4. S9 was applied 10 minutes before AEA. C. Quantification of response. n=45-50 cell.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound represented by Formula (I)

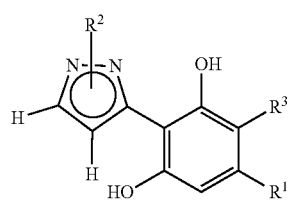

Formula (I)

or a tautomer, a pharmaceutically acceptable salt or solvate thereof; wherein:
$R^1$ is selected from the group consisting of hydrogen and a substituted or unsubstituted alkyl;
$R^2$ is selected from the group consisting of substituted or unsubstituted $C_1$-$C_6$ alkyl, substituted or unsubstituted $C_5$-$C_{20}$ aryl, substituted or unsubstituted arylalkyl, substituted or unsubstituted cycloalkyl, and substituted or unsubstituted heterocyclic ring; and
$R^3$ is selected from the group consisting of hydrogen and halogen.

2. A compound of claim 1, wherein the compound is selected from the group consisting of a compound represented by Formula (II),

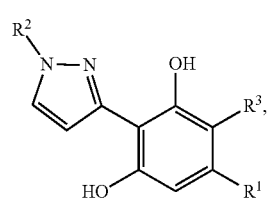

Formula (II)

or a tautomer, a pharmaceutically acceptable salt or solvate thereof, and a compound represented by Formula (III),

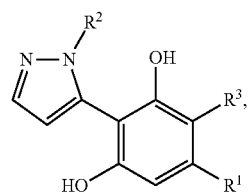

Formula (III)

or a tautomer, a pharmaceutically acceptable salt or solvate thereof,
wherein $R^1$ is selected from the group consisting of hydrogen and a substituted or unsubstituted alkyl;
$R^2$ is selected from the group consisting of substituted or unsubstituted $C_1$-$C_6$ alkyl, substituted or unsubstituted C5-C20 aryl, substituted or unsubstituted arylalkyl, substituted or unsubstituted cycloalkyl, and substituted or unsubstituted heterocyclic ring; and
$R^3$ is selected from the group consisting of hydrogen and halogen.

3. A compound of claim 1, wherein $R^1$ is selected from the group consisting of hydrogen, methyl, pentyl, and 1,1-dimethyl heptyl.

4. A compound of claim 1, wherein $R^2$ is selected from the group consisting of methyl, ethyl, iso-propyl, and tert-butyl.

5. A compound of claim 1, wherein $R^2$ is cyclohexyl.

6. A compound of claim 1, wherein $R^2$ is a phenyl.

7. A compound of claim 6, wherein $R^2$ is a phenyl substituted by a hydroxyl or a methoxy group.

8. A compound of claim 1, wherein $R^2$ is a substituted or unsubstituted benzyl.

9. A compound of claim 1, wherein $R^3$ is selected from the group consisting of hydrogen and fluorine.

10. A compound of claim 1, wherein the compound is selected from the group consisting of:
5-pentyl-2-(1-phenyl-1H-pyrazol-5-yl)benzene-1,3-diol,
2-(1-methyl-1H-pyrazol-5-yl)-5-pentylbenzene-1,3-diol,
2-(1-benzyl-1H-pyrazol-3-yl)-5-pentylbenzene-1,3-diol,
2-(1-benzyl-1H-pyrazol-5-yl)-5-pentylbenzene-1,3-diol,
2-(1-isopropyl-1H-pyrazol-5-yl)-5-pentylbenzene-1,3-diol,
2-(1-isopropyl-1H-pyrazol-5-yl)-5-(2-methyloctan-2-yl)benzene-1,3-diol,
2-(1-isopropyl-1H-pyrazol-3-yl)-5-(2-methyloctan-2-yl)benzene-1,3-diol,
2-(1-isopropyl-1H-pyrazol-3-yl)benzene-1,3-diol, 12-(1-isopropyl-1H-pyrazol-5-yl)benzene-1,3-diol, 2-(1-isopropyl-1H-pyrazol-3-yl)-5-methylbenzene-1,3-diol,
2-(1-isopropyl-1H-pyrazol-5-yl)-5-methylbenzene-1,3-diol,
2-(1-isopropyl-1H-pyrazol-3-yl)-5-pentylbenzene-1,3-diol,
2-(1-benzyl-1H-pyrazol-3-yl)-5-methylbenzene-1,3-diol,
2-(1-benzyl-1H-pyrazol-5-yl)-5-methylbenzene-1,3-diol,
2-(1-cyclohexyl-1H-pyrazol-5-yl)-5-pentylbenzene-1,3-diol,
2-(1-(tert-butyl)-1H-pyrazol-3-yl)-5-pentylbenzene-1,3-diol,
2-(1-(tert-butyl)-1H-pyrazol-5-yl)-5-pentylbenzene-1,3-diol,
2-(1-ethyl-1H-pyrazol-3-yl)-5-pentylbenzene-1,3-diol,
2-(1-ethyl-1H-pyrazol-5-yl)-5-pentylbenzene-1,3-diol,
2-(1-cyclohexyl-1H-pyrazol-3-yl)-5-methylbenzene-1,3-diol,
2-(1-cyclohexyl-1H-pyrazol-5-yl)-5-methylbenzene-1,3-diol,
2-(1-ethyl-1H-pyrazol-3-yl)-5-methylbenzene-1,3-diol,
2-(1-ethyl-1H-pyrazol-5-yl)-5-methylbenzene-1,3-diol,
5-methyl-2-(1-(pyridin-4-ylmethyl)-1H-pyrazol-5-yl)benzene-1,3-diol,
2-(1-benzyl-1H-pyrazol-3-yl)-4-fluoro-5-pentylbenzene-1,3-diol,
2-(1-(3-hydroxybenzyl)-1H-pyrazol-3-yl)-5-pentylbenzene-1,3-diol,
2-(1-(3-hydroxybenzyl)-1H-pyrazol-5-yl)-5-pentylbenzene-1,3-diol,
2-(1-(4-hydroxybenzyl)-1H-pyrazol-5-yl)-5-pentylbenzene-1,3-diol, and
2-(1-(4-hydroxybenzyl)-1H-pyrazol-3-yl)-5-pentylbenzene-1,3-diol.

11. A pharmaceutical composition comprising at least one compound of claim 1.

12. A method of treating a disease or disorder associated with GPR18 receptor, the method comprising administering the compound of claim 1 or a composition thereof,
wherein the disease or disorder associated with GPR18 receptor is selected from the group consisting of neurodegenerative diseases, endometriosis, peritonitis, metabolic dysfunction, obesity-related disease, diabetes, bacterial infection, cardiovascular disease, pain, glaucoma, metastatic melanoma, and male reproduction.

13. A method of treating a disease or disorder associated with TRPV1 receptor, the method comprising administering the compound of claim 1 or a composition thereof,
wherein the disease or disorder associated with TRPV1 receptor is selected from the group consisting of pain, diabetes type-2, epilepsy, anxiety, depression, and drug-addiction.

14. A composition comprising at least one compound of claim 1.

15. A compound selected from the group consisting of:
5-pentyl-2-(1-phenyl-1H-pyrazol-5-yl)benzene-1,3-diol,
2-(1-methyl-1H-pyrazol-5-yl)-5-pentylbenzene-1,3-diol,
2-(1-benzyl-1H-pyrazol-3-yl)-5-pentylbenzene-1,3-diol,
2-(1-benzyl-1H-pyrazol-5-yl)-5-pentylbenzene-1,3-diol,
5-(2-methyloctan-2-yl)-2-(1H-pyrazol-3-yl)benzene-1,3-diol,
2-(1-isopropyl-1H-pyrazol-5-yl)-5-pentylbenzene-1,3-diol,
2-(1-isopropyl-1H-pyrazol-5-yl)-5-(2-methyloctan-2-yl)benzene-1,3-diol,
2-(1-isopropyl-1H-pyrazol-3-yl)-5-(2-methyloctan-2-yl)benzene-1,3-diol,
2-(1-isopropyl-1H-pyrazol-3-yl)benzene-1,3-diol,
2-(1-isopropyl-1H-pyrazol-5-yl)benzene-1,3-diol,
2-(1-isopropyl-1H-pyrazol-3-yl)-5-methylbenzene-1,3-diol,
2-(1-isopropyl-1H-pyrazol-5-yl)-5-methylbenzene-1,3-diol,
2-(1-isopropyl-1H-pyrazol-3-yl)-5-pentylbenzene-1,3-diol,
2-(1-benzyl-1H-pyrazol-3-yl)-5-methylbenzene-1,3-diol,
2-(1-benzyl-1H-pyrazol-5-yl)-5-methylbenzene-1,3-diol,
2-(1-cyclohexyl-1H-pyrazol-5-yl)-5-pentylbenzene-1,3-diol,
2-(1-(tert-butyl)-1H-pyrazol-3-yl)-5-pentylbenzene-1,3-diol,
2-(1-(tert-butyl)-1H-pyrazol-5-yl)-5-pentylbenzene-1,3-diol,
2-(1-ethyl-1H-pyrazol-3-yl)-5-pentylbenzene-1,3-diol,
2-(1-ethyl-1H-pyrazol-5-yl)-5-pentylbenzene-1,3-diol,
5-methyl-2-(1H-pyrazol-3-yl)benzene-1,3-diol,
2-(1-cyclohexyl-1H-pyrazol-3-yl)-5-methylbenzene-1,3-diol,
2-(1-cyclohexyl-1H-pyrazol-5-yl)-5-methylbenzene-1,3-diol,
2-(1-ethyl-1H-pyrazol-3-yl)-5-methylbenzene-1,3-diol,
2-(1-ethyl-1H-pyrazol-5-yl)-5-methylbenzene-1,3-diol,
5-methyl-2-(1-(pyridin-4-ylmethyl)-1H-pyrazol-5-yl)benzene-1,3-diol,
2-(1-benzyl-1H-pyrazol-3-yl)-4-fluoro-5-pentylbenzene-1,3-diol,
2-(1-(3-hydroxybenzyl)-1H-pyrazol-3-yl)-5-pentylbenzene-1,3-diol,
2-(1-(3-hydroxybenzyl)-1H-pyrazol-5-yl)-5-pentylbenzene-1,3-diol,
2-(1-(4-hydroxybenzyl)-1H-pyrazol-5-yl)-5-pentylbenzene-1,3-diol, and
2-(1-(4-hydroxybenzyl)-1H-pyrazol-3-yl)-5-pentylbenzene-1,3-diol.

16. The compound of claim 1, wherein the substituted or unsubstituted alkyl is a substituted or unsubstituted alkyl $C_1$-$C_9$ alkyl.

17. The compound of claim 2, wherein the substituted or unsubstituted alkyl is a substituted or unsubstituted alkyl $C_1$-$C_9$ alkyl.

* * * * *